United States Patent [19]
Kolber et al.

[11] Patent Number: 5,426,306
[45] Date of Patent: Jun. 20, 1995

[54] FAST REPETITION RATE (FRR) FLUOROMETER AND METHOD FOR MEASURING FLUORESCENCE AND PHOTOSYNTHETIC PARAMETERS

[75] Inventors: Zbigniew Kolber, Shoreham; Paul Falkowski, Stony Brook, both of N.Y.

[73] Assignee: Associated Universities, Inc., Washington, D.C.

[21] Appl. No.: 138,984

[22] Filed: Oct. 21, 1993

[51] Int. Cl.6 .................................. G01N 21/64
[52] U.S. Cl. .................... 250/458.1; 250/459.1; 250/461.1
[58] Field of Search ............ 250/458.1, 459.1, 461.1, 250/461.2

[56] References Cited
U.S. PATENT DOCUMENTS

| | | |
|---|---|---|
| 3,666,945 | 5/1972 | Frungel et al. . |
| 4,084,905 | 4/1978 | Schreiber et al. . |
| 4,178,512 | 12/1979 | Frungel et al. . |
| 4,293,225 | 10/1981 | Wheaton . |
| 4,650,336 | 3/1987 | Moll . |
| 4,698,308 | 10/1987 | Ikeda . |
| 4,730,922 | 3/1988 | Bach et al. . |
| 4,786,813 | 11/1988 | Svanberg et al. . |
| 4,802,768 | 2/1989 | Gifford et al. . |
| 4,804,849 | 2/1989 | Booth et al. . |
| 4,804,850 | 2/1989 | Norrish et al. . |
| 4,840,485 | 6/1989 | Gratton . |
| 5,075,714 | 12/1991 | Hagiuda et al. . |
| 5,107,292 | 4/1992 | Tanaka et al. . |
| 5,130,738 | 7/1992 | Hirata . |
| 5,159,381 | 10/1992 | Harrison . |
| 5,180,953 | 1/1993 | Hirata et al. . |
| 5,184,171 | 2/1993 | Uenishi . |
| 5,187,410 | 2/1993 | Shimizu et al. . |
| 5,323,008 | 6/1994 | Studholme et al. .......... 250/459.1 |

OTHER PUBLICATIONS

Ortner, "Integration of a Sea-Martec Fluorometer to a Towed Plankton Camera", Biowatt News, Nov. 1987.
Falkowski, et al., "Relationship of Steady-State Photosynthesis to Fluorescence in Eucaryotic Algae", Biochimica et Biophysica Acta, 849, 1986, 183-192.
Kolber, et al., "Fast Repetition Rate (FRR) Fluorometer for Making in situ Measurements of Primary Productivity", presented at OCEANS 92-Mastering the Oceans Through Technology, Newport, R.I., Oct. 26-29, 1992.
BNL 49309, "Physiological Limitation of Phytoplankton Photosynthesis in the Eastern Equatorial Pacific Determined from Natural Variability in the Quantum Yield of Flourescence", Brookhaven National Laboratory, Upton, N.Y. 11973, Jul. 1993.

Primary Examiner—Paul M. Dzierzynski
Assistant Examiner—Richard Hanig
Attorney, Agent, or Firm—Margaret C. Bogosian

[57] ABSTRACT

A fast repetition rate fluorometer device and method for measuring in vivo fluorescence of phytoplankton or higher plants chlorophyll and photosynthetic parameters of phytoplankton or higher plants by illuminating the phytoplankton or higher plants with a series of fast repetition rate excitation flashes effective to bring about and measure resultant changes in fluorescence yield of their Photosystem II. The series of fast repetition rate excitation flashes has a predetermined energy per flash and a rate greater than 10,000 Hz. Also, disclosed is a flasher circuit for producing the series of fast repetition rate flashes.

28 Claims, 10 Drawing Sheets

FAST REPETITION RATE (FRR) FLUOROMETER AND METHOD FOR MEASURING FLUORESCENCE AND PHOTOSYNTHETIC PARAMETERS

This invention was made with Government support under contract number DE-AC02-76CH00016, between the U.S. Department of Energy and Associated Universities, Inc. The Government has certain rights in the invention.

FIELD OF THE INVENTION

The present invention relates generally to fluorometers, instruments for measuring wavelength and intensity of fluorescence. More particularly, this invention relates to a device and method for measuring in vivo fluorescence of phytoplankton or higher plants chlorophyll and photosynthetic parameters of phytoplankton or higher plants by illuminating the phytoplankton or higher plants with a series of fast repetition rate excitation flashes to bring about and measure resultant changes in fluorescence yield.

BACKGROUND OF THE INVENTION

Measurement of photosynthetic activity that occurs in photosynthetic organisms such as phytoplankton or higher plants is important to understanding phytoplankton and higher plants basic physiology, as well as in ecological studies of the environmental stress. For instance, in ocean studies, measurement of photosynthesis of phytoplankton is useful in understanding the ocean carbon cycle and predicting how climate-induced changes in ocean circulation, as well as, anthropogenic perturbation affect ocean productivity, and vice versa, how the oceans can mediate the climate change. Assessment of photosynthesis by photosynthetic organisms requires either a direct measurement, or an indirect approach based on measurement of photosynthetic parameters.

Direct measurements of photosynthesis of phytoplankton or higher plants include those of $CO_2$ exchange, $O_2$ evolution, or radioactive labelled carbon incorporation (i.e., $^{14}C$ method). However, these measurements are laborious, time consuming, and not applicable in certain conditions. In studying phytoplankton, the $^{14}C$ measurement method requires an incubation and can be done only for discrete, bottled samples. Further, accuracy in photosynthesis measurements of phytoplankton in laboratory settings are limited as a result of removal of the phytoplankton from its normal ambient nutrient flux, and laboratory simulation of ambient light and temperature conditions.

Indirect measurements of photosynthesis, based on a functional relationship between photosynthetic activity and fluorescence, have proven to be more successful. Such indirect measurement methods include both passive fluorescence and active fluorescence techniques. Passive fluorescence techniques are based on measurement of solar induced fluorescence and utilize photosensors for detecting both fluorescence and ambient solar irradiance.

An example employing the passive fluorescence technique is described in U.S. Pat. No. 4,804,849 granted to Booth et al. which discloses an apparatus for optically measuring scalar irradiance or incident flux of radiant energy and for optically measuring naturally occurring chlorophyll fluorescence or upwelling radiance from photosynthetic organisms in a parcel of water in a natural setting. Computer means are used for comparing those two measurements and for determining the concentrations of chlorophyll and calculating the rate of primary photosynthetic production. Unfortunately, passive fluorescence techniques are flawed by an assumption that the ratio of the photosynthetic to fluorescence yield is constant. In nature, this ratio can vary by as much as 10:1, making the passive based estimates of photosynthesis unreliable. More detailed measurement and study of photosynthetic processes, such as light absorption, primary photochemistry, and electron transport between so-called Photosystem II (PSII), and Photosystem I (PSI), are not possible with passive fluorescence techniques.

Active fluorescence techniques, on the other hand, are based on flash stimulated fluorescence. An example employing an active fluorescence technique, is contained in U.S. Pat. No. 4,650,336 granted to Moll which discloses a method and device for measuring photosynthesis, specifically variable fluorescence of plants. Variable fluorescence is measured as the difference between a low level, steady state fluorescence and a higher level of a fluorescent transient. The fluorometer device disclosed by Moll has one lamp to provide constant-level light to bring about continuous, steady state fluorescence of a plant, and a flash lamp to provide a flash of light (excitation energy) to bring about a transient fluorescence of the plant. The device and method of Moll utilize the second flash lamp to produces either a single flash, or series of flashes at slow repetition rate, approximately one hundred (100) Hz. Even at 100 Hz the flash rate is too slow to effectively measure the faster photosynthetic processes occurring in photosynthetic organisms.

Another active fluorescence technique is described in our earlier U.S. Pat. No. 4,942,303. That technique enables more detailed measurement of photosynthesis. Specifically, our active fluorescence technique involves use of "pump and probe" flashes for measuring the change in fluorescence of phytoplankton or higher plants. A relatively low intensity probe flash is followed quickly by a pump flash that is usually made intense enough to saturate PSII. Also disclosed in that earlier patent is a computer controlled fluorometer device and method that efficiently and accurately measures photosynthesis by precisely monitoring and recording changes in fluorescence produced by a computer controlled series of cycles of probe and pump flashes. From these measurements various photosynthetic parameters relating to the faster photosynthetic processes can be determined and incorporated into a mechanistic model of photochemistry based on the kinetics of electron flow between Photosystems II and I. The pump and probe technique, although very successful in measuring the photosynthesis occurring in phytoplankton or higher plants, has the following operational limitations:

1. In order to measure the absorption cross-section and the rate of electron flow from PSII to PSI the pump and probe fluorometer employs a sequence of probe, pump, and probe flashes, repeated up to 30 times, with the intensity of the pump flash changed from zero to a supersaturating level, or with the delay between the pump, and the second probe flash changing from 80 $\mu s$ to 300 ms. These two protocols require 5 minutes to 10 minutes of fluorometer operation in order to make appropriate measurements. Particularly, when the pump and probe technique is used in a profiling mode for studying phytoplankton in the ocean, where these protocols often have to be executed at every meter of a water column, the time required for making the measurements is prohibitively long.

2. The intensity of the probe flash has to be kept below 1% of the PSII saturation level. This low intensity flash results in a low signal to noise ratio, particularly at low chlorophyll concentrations.

3. The pump and probe fluorometer requires two separate excitation channels (i.e., two flashers) which complicates construction, and increases the cost of the fluorometer.

4. Execution of a full experimental protocol, particularly in studying phytoplankton in the ocean, utilizes a large amount of electrical power. This requirements limits long-term, remote mooring applications where electrical batteries are used to power the fluorometer.

Another factor limiting active fluorescence techniques for study and measurement of photosynthesis is the current state of the art of flash lamps and flasher circuits. Specifically, many state of the art flash lamps and flasher circuits operate at too slow a repetition rate to permit accurate and rapid measurement of the faster (100 μs to 300 ms) photosynthetic processes.

For studying photosynthesis, xenon flash lamps are a preferred source of excitation light for use in active fluorescence techniques because of their ability to produce a bright and very broad spectral range of light with high efficiency. Xenon flash lamps typically are operated to generate a flash of light when energy stored in an associated capacitor is discharged. Discharge is initiated by a triggering spark generated by a high voltage (5-15 kV) pulse prior to the flash. Generally, once triggered the flash lamp uses all the energy stored in the discharge capacitor. The light intensity of the flash is proportional to the stored energy, E, which is a function of capacitance, C, and the voltage, V, ($E = 0.5 V^2 C$). The energy of the flash can be controlled by varying the voltage on the discharge capacitor. To generate a subsequent flash, it is necessary to recharge the capacitor, which requires prior cooling of the plasma in the flash lamp. This limits the frequency of flashes to less than one hundred (100) Hz, or 10 ms minimum time delay between pulses (Cramer and Crofts. Photosynthesis Research 23, 231-240, 1990).

One attempt to produce a series of flashes at a rate faster than one hundred (100) Hz has included a bank, or a plurality, of flash lamps each with separate discharge capacitors. This solution requires complicated optics for directing the flash light onto a target or sample. Although a high rate of flashes can be produced by suitably sequencing ignition of the bank of flash lamps, there is an upper limit achievable based on the number of flash lamps. Additionally, the energy of the flashes cannot be changed unless a separate high voltage power supply with controlled voltages is used. This approach results in a large, complicated and costly fluorometer design.

In the field of cameras, flashing circuits have been devised using linear xenon flash lamps and Insulated Gate Biploar Transistors (IGBT) to more efficiently control a single high speed flash that is useful for photographing a subject. In these applications, control of the time for switching the flash lamp ON and OFF permits illumination of a photographed object with a precisely dosed amount of light. Usually, after switching the lamp ON, a photodiode measures the amount of light delivered to the photographed object, and generates an OFF signal after sufficient exposure. In these applications the triggering signal is either generated by the same type of IGBT transistor, as disclosed in U.S. Pat. No. 5,187,410 granted to Shimizu et al., or by using a standard thyristor circuit as disclosed in U.S. Pat. No. 5,159,381 granted to Harrison. Other examples, such as U.S. Pat. No. 5,107,292 granted to Tanaka et al. and U.S. Pat. No. 5,184,171 granted to Uenishi, describe the use of an IGBT that is switched ON before the triggering signal, thus reducing the high voltage on the collector of the IGBT before switching ON. In U.S. Pat. No. 5,075,714 granted to Hagiuda et al., an IGBT switch allows a doubling of the high voltage of the flash lamp at the end of the lamp ON state, thus reducing the high voltage rating of the charging circuitry. Another example U.S. Pat. No. 5,130,738 granted to Hirata uses an IGBT to deionize a flash lamp following switching of the lamp OFF. Switching the lamp OFF with an IGBT after a flash, stops the current flow through the lamp, allowing both the deionization of the lamp and instant recharging of the discharge capacitor. These examples disclose circuitry for delivering a single flash, and none of the examples disclose circuitry for producing and controlling a series of fast repetition rate flashes.

In another invention in U.S. Pat. No. 5,180,953 granted to Hirata et al., a strobe device uses a step-up capacitor connected to a flash discharge tube which is charged by current flowing through the tube. Thus, the device realizes a rapid charging of its step-up capacitor resulting in repeated high-speed luminous emissions of several tens of Hz (i.e., approximately 20 Hz to 30 Hz), which is not nearly fast enough for studying the faster processes of photosynthesis.

Thus, there is the need for a Fast Repetition Rate Fluorometer operable to produce a series of fast repetition rate flashes in the range of the faster processes of photosynthesis, i.e. 10,000 Hz to 250,000 Hz and at controlled energies sufficient to gradually and incrementally effect the faster photosynthetic processes occurring in PSII and PSI in phytoplankton or higher plants, for accurate and rapid measurement of fluorescence with high signal to noise ratios and determination of photosynthetic parameters.

SUMMARY OF THE INVENTION

Accordingly, it is an object of the present invention to provide a fast repetition rate fluorometer that is operable to provide a number of different measurements of photosynthesis by means of precisely monitoring changes in fluorescence and fluorescence yield in phytoplankton or higher plants in response to a series of fast repetition rate excitation flashes.

It is also an object of the present invention to provide a fast repetition rate fluorometer that is operable to provide a series of controlled energy and fast rate excitation flashes to gradually and incrementally saturate the Photosystem II in phytoplankton and higher plants to provide rapid and accurate measurement of photosynthetic parameters such as variable fluorescence, effective absorption cross-section, rates of electron flow between PS II and PS I, and turnover time of photosynthesis.

It is another object of the invention to provide a fast repetition rate fluorometer that can independently measure the Plastoquinou (PQ)-pool size and the concentration of PSII reaction centers, in phytoplankton and higher plants.

It is a further object of the invention to provide a fast repetition rate fluorometer that is computer controlled and has a significantly shortened experimental protocol for producing a series of controlled energy and rate excitation flashes for the study of photosynthesis in phytoplankton and higher plants.

Another object of the invention is to provide a fast repetition rate fluorometer having a high signal to noise ratio that permits more robust measurements to be made, particularly in the study of phytoplankton in open sea environments with low chlorophyll concentrations, i.e., in the range of about 0.05 $\mu g$/liter.

Yet another object of the invention to provide a fast repetition rate fluorometer to enable measurement of the on-going photosynthetic parameters and photosynthetic rates of phytoplankton and higher plants under both darkness and ambient irradiance conditions, and configured either for use as a laboratory bench top model, or as a submersible model for, in situ, use in the ocean.

A further object of the present invention to provide a fast repetition rate fluorometer which is simple in construction and which may be manufactured relatively easily and inexpensively for widespread use in physiological and environmental scientific research.

Still another object of the present invention is to provide a method of illuminating a sample of phytoplankton or higher plants with a series of fast repetition rate excitation flashes, measuring the energy of the excitation flashes and fluorescence from the sample, and determining photosynthetic parameters from those measurements.

It will be noted that this present invention is not limited to its application to measurement of fluorescence solely in photosynthetic organisms, but may be applied to any situation where a series of fast repetition rate flashes permit in-depth and detailed study of processes such as chemical or biological analyses based on fluorescence.

Additional objects and advantages of the invention will become apparent from the description of it presented below.

Certain of the foregoing and related objects are also readily obtained in the method of the invention for measuring phytoplankton or higher plants photosynthetic parameters, comprising the steps of generating fast repetition rate flashes, acquiring fluorescence yield data, and processing the data according to a numerical model describing the kinetics of light absorption and electron transport from PSII to PSI.

DESCRIPTION OF THE DRAWINGS

Other objects and features of the present invention will become apparent from the detailed description considered in connection with the accompanying drawings, which disclose several embodiments of the invention. It is to be understood that the drawings are to be used for the purpose of illustration only and not as a definition of the limits of the invention.

In the drawings, wherein similar reference characters denote similar elements throughout the several views.

DESCRIPTION OF THE INVENTION

Figure 1:
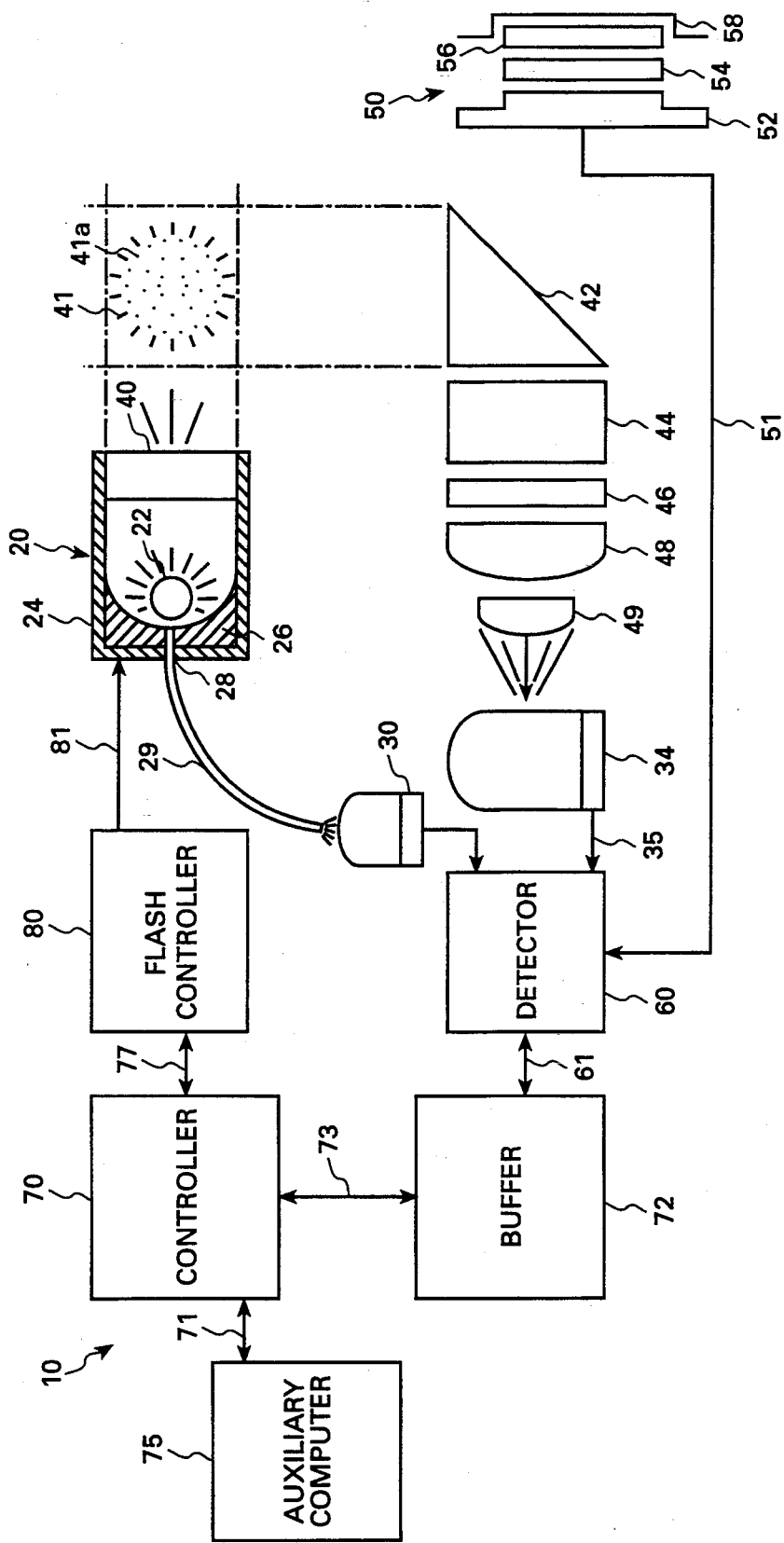
FIG. 1 is a schematic circuit diagram and associated optical apparatus of a fast repetition rate fluorometer embodying the present invention.

Turning now in detail to the drawings and particularly to FIG. 1, there is illustrated a schematic diagram of a Fast Repetition Rate (FRR) Fluorometer 10 embodying the present invention. FRR Fluorometer 10 is capable of measuring change in fluorescence of a sample of phytoplankton or higher plant in darkness or under background illumination, and includes flasher means for producing a series of fast repetition rate flashes at a rate greater than 10,000 Hz to effect fluorescence in the sample, and also includes measuring means for measuring fluorescence of the sample as a function of the excitation energy produced by flashes.

The illustrated flasher means used for producing a series of fast repetition rate flashes at a rate greater than 10,000 Hz generally includes a single flasher 20, an excitation filter 40, a controller 70, and a flash control unit 80. Flasher 20 provides a series of fast repetition rate excitation flashes to selectively and controllably bring about fluorescence of a sample of phytoplankton or higher plants 41a contained in a sample volume 41 (outlined by the crossing, dashed lines). Flasher 20, preferably includes a xenon linear flash lamp 22 capable of efficiently generating a bright and broad spectral range of light, although xenon flashbulbs are also suitable. A suitable flash lamp 22 can be purchased from EG&G, Inc., as its model FXG-33C-15, and xenon flashbulbs can be purchased from EG&G, Inc., model 9B and 12B series, or from Hamamatsu Corporation, models L21, L23, and L24. The series of fast repetition rate excitation flashes is controlled by controller 70 and flash control unit 80 (both described in more detail below) operatively connected to flasher 20 by cable 81.

Flash lamp 22 is preferably disposed in a holder 24 that permits the flashes to pass through excitation filter 40 while preventing unfiltered excitation flashes from contaminating or interfering with the detection and measurement of fluorescence from the phytoplankton or higher plants sample 41a. Holder 24 is made of light absorbing material such as black plastic, sold under the trademark DELRIN, available from AIN Plastics, Inc. At the base of holder 24 is preferably a parabolic mirror 26 that increases the effective energy of the excitation flashes by reflecting and focusing the excitation light toward excitation filter 40. Mirror 26 can be cut of nickel blank, electropolished, and electroplated with Rhodium. Rhodium exhibits high reflectance at high incidence angles particularly in the spectral range of 300 to 600 nanometers (nm), as well as high mechanical surface resistance to scratches and abrasion. Mirror 26, besides reflecting excitation flashes, also serves as an external triggering electrode (described in more detail below), resulting in a compact flasher design.

The series of excitation flashes produced by flash lamp 22 passes through excitation filter 40, before entering sample volume 41. In studying phytoplankton, red light at a wavelength of 683 nm, is filtered from the excitation flashes by excitation filter 40 so as to not enter the sample volume 41 and contaminate or interfere with the observable fluorescence emitted from the sample of phytoplankton of higher plant at the same wavelength. In addition, in the case of studying phytoplankton, filter 40 should selectively pass the light of spectral quality similar to sunlight observed in ocean water. Preferably, a combination of blue-green filters having a broad-band and low-pass are used in excitation filter 40 to select a 400 to 520 nm excitation bandwidth of wavelengths. A 12 mm thick filter, or a stack or four, 3 mm thick filters, provides a sufficient level of filtering of the excitation flashes by excitation filter 40, and can be purchased from Shott Glaswerke (Germany), model BGI-39.

Referring still to FIG. 1, measuring means for measuring fluorescence of sample 41a as a function of the series of repetition rate flashes includes generally; an emission filter 46, and an emission photodetector 34. Preferably, the measuring means also includes a prism 42 and a suitable conventional collimator 44. Prism 42 redirects the fluorescence 90 degrees toward the collimator 44, enabling a compact FRR Fluorometer design in that the excitation flashes and the fluorescence to be measured for sample 41a travel in opposite parallel directions. Prism 42 can be purchased from Edmund Scientific, Inc., model number 32528.

Collimator 44 is made from a block of DELRIN with parallel holes (not drawn) extending therethrough between prism 42 and excitation filter 46. Fluorescence emitted from sample 41a in a direction perpendicular to surface 42a of prism 42 is effectively reflected to pass through collimator 44 and reach emission filter 46. Fluorescence and excitation flashes emitted in a direction not perpendicular to surface 42a will not travel along the parallel holes in collimator 44 and will be absorbed.

Emission filter 46 filters out scattered excitation light, and permits only the fluorescence from phytoplankton or higher plants sample 41a to pass through for detection by emission photodetector 34. Emission filter 46 is a combination of low-pass cut-off color glass filter and interference bandpass filter. For the study of phytoplankton commercially available filters from Shott, model RG665, and a pair of 10 nm bandpass interference filters centered on 680 nm, commercially available from Corion Corporation, model S10-680-R, can be used, or preferably, an excitation filter can be custom designed and made by Corion centered at 683 nm.

To increase the efficiency of detection, condenser lenses 48 and 49 focus the filtered fluorescence light onto a conventional photocathode (not shown) of emission photodetector 34. The lenses, respectively, are available from Melles Griot, model OILPXIII and Melles Griot, model OILCP127.

Photodetector 34 detects the fluorescence light and produces a corresponding electrical analog signal. Photodetector 34 preferably includes a photomultiplier with a photocathode of the multi-alkali type that has high quantum efficiency at 683 nm which corresponds to the fluorescence emitted from the sample of phytoplankton. The filtered fluorescence signal from photodetector 34 is delivered to detector circuit 60 by shielded cable 35. A suitable conventional photodetector or photodiode can be purchased from Hamamatsu, EG&G, or United Detector Technology. The photomultiplier used in the disclosed fluorometer is Hamamatsu, R928. A Hamamatsu, C2456, subminiature modular power supply (not shown) is operatively connected to and provides the high voltage required for proper operation of photodetector 34. The gain of the photomultiplier (in 34) is controlled by varying the high voltage supplied from the power supply in the range of 300 to 1100 volts. A controlling voltage of the high voltage power supply, in the range 0.0 to 1.5 V, is provided by a digital to analog converter (D/A) (Analog Devices AD7226) (not shown). Although, the filtered fluorescence signal can be outputted to a host computer, preferably it is converted to digital form by detector circuitry 60, reduced and stored in the buffer 72, for subsequent measurement, as described in greater detail below.

In a preferred embodiment of the invention for rapidly and accurately making measurements of various photosynthetic parameters of the sample 41a, fluorometer 10 further includes a second measuring means for measuring the energy of the excitation flashes (a reference channel). The second measuring means includes an excitation photodetector 30, and a light guide 28 (preferably a fiber optic cable) passing through a 3 mm diameter orifice 29 in holder 24 transporting approximately 2% of the energy of the excitation flashes to excitation photodetector 30. A suitable photodetector or photodiode for this purpose can be purchased from Hamamatsu, EG&G, or United Detector Technology. The excitation photodiode (30) used in the disclosed fluorometer is Hamamatsu S2386-SK, to produce an electrical analog signal proportional to the energy of the series of fast repetition rate excitation flashes produced by flash lamp 22.

Still referring to FIG. 1, a third photodetector, Photosynthetic Active Radiation (PAR) sensor 50, can be used to detect the ambient irradiance that is received by the phytoplankton or higher plant sample 41a being studied. The sensor 50 can be designed by one skilled in the art using a photodiode 52 with a color conversion filter 54, or a suitable conventional sensor may be purchased from Biospherical, Inc. PAR sensor 50 includes a Teflon (TM of DuPont Corporation) light diffuser 56 positioned before filter 54, and covered by a clear acrylic cap 58. Preferably, a 2 mm thick blue color conversion filter available from Shott Glaswerke, model FG6 results in detection of ambient light in the range of 400–700 nm (i.e., ocean sunlight). The ambient irradiance signal from photodiode 52 is delivered to detector circuit 60 by shielded cable 51.

Detector circuit 60 is used to condition and to convert to digital form the analog signals of the filtered fluorescence signal, fast repetition rate excitation flashes, and the ambient irradiance from, respectively, photodetectors 34, 30, and PAR sensor 50. The operation of detector circuit 60 is controlled by controller 70 through cable 73 to data buffer 72 and cable 61. For conditioning the filtered fluorescence signal, and the flash lamps excitation signal, a simple signal conditioning unit based on peak detection of the signals from emission photodetector 34 and excitation photodetector 30, and direct analog/digital conversion, using a conventional A/D converter, can be easily designed for detector circuit 60 by one skilled in the art. However, in the disclosed invention, for conditioning the filtered fluorescence signal and excitation signal there is disclosed below a means to enable a 5 to 10 fold increase in the signal to noise ratio observed in cases of low chlorophyll concentration such as in measurement of phytoplankton, i.e., in the range of 0.05 to 0.5 $\mu$gram/liter of chlorophyll.

For conditioning the filtered fluorescence signal, a first amplifier, type OPA-637 amplifier, available from Analog Devices, Inc. is used in detector circuit 60 with an input of the amplifier connected to the corresponding output of photodetector 30. Next the signal is converted to digital form by an Analog to Digital (A/D) converter. The choice of the A/D converter should be carefully made to satisfy the required conversion speed, resolution, and power consumption for selected applications. A preferred converter for use in detector circuit 60 is a AD875, from Analog Devices, which features a 15 MHz conversion rate, 10 bit resolution, and about 160 milliwatts of active power consumption. The conversion rate is controlled in detector circuit 60 by a conventional clock generator, which can be easily designed by one skilled in the art. A similar set-up for conditioning the filtered fluorescence signal is employed for conditioning the excitation signal.

For conditioning the PAR signal from PAR sensor 50, an amplifier LTCI050, from Linear Technology Corporation, is configured as a current/voltage converter in detector circuit 60. The output voltage signal from the converter is then converted in detector circuit 60 to digital form by an A/D converter, Max 132, from Maxxim Corporation.

The digital signals outputted on line 61 from digital circuit 60, are then supplied to data buffer 72, which features three channels of 64 k$\times$16 bit RAM. Data buffer 72 operates as a fast, scratchpad memory. It accepts the digitized fluorescence and reference signals at 10 MHz conversion rate during flashes. After completion of the flashing sequence, information from the data buffer is downloaded to the controller 70 at a slower rate, determined by the memory cycle of the controller 70.

Referring still to FIG. 1, controller 70 controls the operation of FRR Fluorometer 10. Specifically, controller 70 controls the excitation flash sequence, data acquisition process and initial data reduction. Operation of controller 70 is performed by a software program. A flow chart describing the program is disclosed below (with reference to FIG. 4). Cable 77 connects controller 70 to flash control unit 80. Controller 70 employs a simple board computer purchased from Onset Computer, model Tattletale 7, which is based on the M68300 microprocessor family.

Digital signals from controller 70 that describe the energy and repetition rate of the fast repetition rate excitation flashes are sent via a data and address bus 71 to a timing circuitry in controller 70, which circuitry is designed around a field programmable logic chip, CLi6000, available from Concurrent Logic, Corporation The pulse modulation signal from the logic chip is then sent on cable 77 to flash control unit 80.

Controller 70 operates at variable clock speed, controlled from the software program in a range of 250 kHz to 16 MHz. The highest clock speed is used during a flashing and data acquisition mode of the FRR Fluorometer 10. At time periods between flashes, the clock is slowed down to 250 kHz, which reduces power consumption. Controller 70 can also be forced into a watchdog controlled sleep mode, resulting in power consumption dropping to 3.5 $\mu$W per hour.

Referring to FIG. 1, a critical and novel aspect of FRF Fluorometer 10 is its flashing means for producing a series of fast repetition rate excitation flashes to very rapidly effect fluorescence in a sample of phytoplankton or higher plants. The novel principle employed in the flashing means for producing fast repetition rate flashes is that as long as the plasma in flash lamp 22 is ionized within 100 $\mu$s following the initial triggering, or after the first flash (i.e., rates greater than 10,000 Hz) the flash lamp 22 can be reignited by a short pulse of high, i.e., 200 to 1000 Amperes, current. In the present invention, flash control unit 80 activates flash lamp 22 by providing approximately 30 to 200 pulses of current at rates up to 250,000 Hz. Specifically, controller 70 provides a pulse-modulation flash control signal via cable 77 to flash controller unit 80 and flash control unit 80 sends corresponding pulses of current via cable 81 to flash lamp 22 for producing a series of fast repetition rate excitation flashes.

Figure 2:
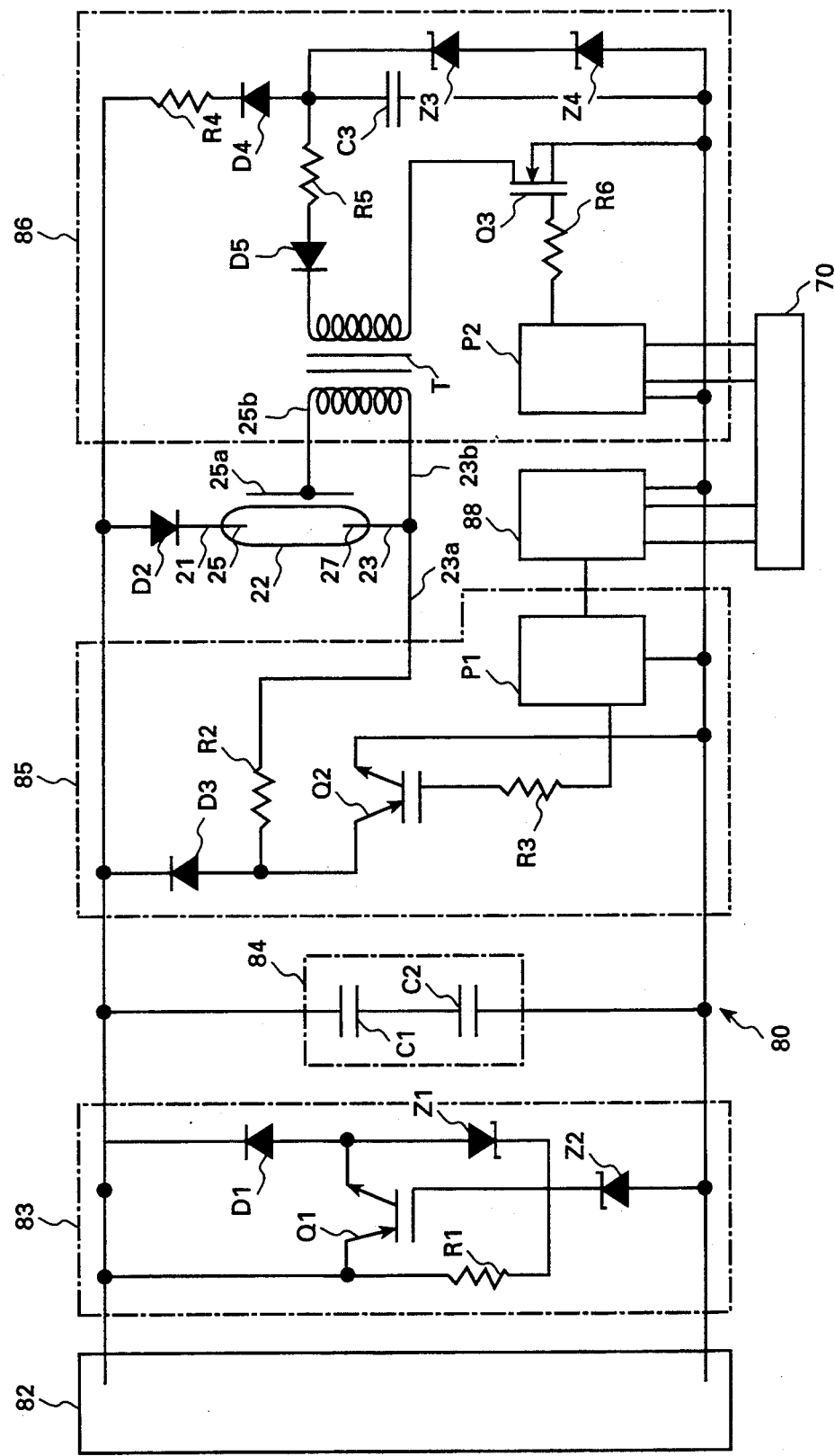
FIG. 2 is a schematic circuit diagram of a flash control unit of the fast repetition rate fluorometer shown in FIG. 1.

Referring now to FIG. 2, flash control unit 80 is shown in greater detail, along with flash lamp 22 and controller 70. Specifically, flash control unit 80 includes a high voltage power supply 82, a charge cut-off switch 83, discharge capacitor 84, current switch 85, trigger circuit 86, and control circuit 88. The high voltage power supply 82 is used to power the various components of flash control unit 80 and can be purchased from EG&G, model PS358 Pulse Pack.

Charge cut-off switch 83 permits controlled charging of discharge capacitor 84 to the proper voltage and includes an Insulated Gate Bipolar Transistor (IGBT) Q1, Zener diode Z1(1N965B) connected to the gate and the emitter of Q1, and a resistor R1 connected to the collector and the gate of Q1. Q1 is open as long as the voltage on the discharge capacitor 84 (C1 and C2), is lower than the voltage on the Zener diode Z2 (2x1N992B, 1N965B) connected to the gate of the IGBT minus voltage on the Zener diode Z1. In the circuitry shown this voltage is preferably set at 400 V, and corresponds to the voltage rating of discharge capacitor 84. Optionally, the cut-off voltage may be varied by varying the voltage on the gate of Q1 using an analog signal from controller 70. A suitable IGBT (for Q1) may be purchased from International Rectifier, Corporation, model IRGPC50U.

Discharge capacitor 84 consists of two discharge capacitors C1 and C2 connected in series with a voltage rating of 400 V. These capacitors store up to 18 Joules of energy. Capacitors C1 and C2 used in this embodiment are manufactured by AVX Corporation, model SM962E367ZAN. The cut-off switch 83 is protected by diode D1 from over-voltage spikes on discharge capacitor 84. The construction of discharge capacitor 84 offers a storage capacitor with high energy density, and low series resistance. As an alternative, a bank of tantalum capacitors can be used, however, at a cost of higher series resistance and higher losses.

Discharge capacitor 84 is connected via diode D2 to a high-voltage terminal 21 of flash lamp 22. The diode D2 (MR760) protects discharge capacitor 84 from the voltage spikes generated by the inductance component of the impedance of flash lamp 22. A low voltage terminal 23 of flash lamp 22 is connected by line 23a to a ballast resistor R2 (and other parallel resistors, not shown) in current switch 85 and by line 23b to a transformer T in trigger circuit 86.

Current switch 85 is a critical component for generation a train of a few hundred flashes with a repetition rate of up to 250 kHz, and current switch 85 is capable of switching currents of up to 1000 Amperes, with less than 200 ns (nanoseconds) rise and tail time, and with low losses. Current switch 85 is composed of five IGBTs connected in parallel and available from International Rectifier Corporation, model IRGPC50U. Only one of the IGBTs, Q2, is shown in FIG. 2. To handle the 1000 Amperes of the required current, each of the five IGBTs handle up to 250 Amperes. To ensure a uniform load on all the IGBTs, 0.25 ohm ballast resistors (only R2 is shown in FIG. 2) are used in a conventional manner. Five 5 ohm base resistors (only R3 is shown in FIG. 2) are connected, respectively to the gate of each IGBT to ensure uniform driving of all the IGBT's from control circuit 88. The current rating of the switch 85 can be increased by paralleling more than five IGBT's, such as Q2. Alternatively, the current switch can use power MOSFET or HEXFET transistors or transistor modules. However, IGBTs are preferred for high voltage applications because of lower ON resistance. The collectors of the IGBTs are protected from over-voltage spikes by shunt diodes (1N4007), of which only D3 is shown in FIG. 2. Current switch 85 is efficiently driven between ON and OFF states by a power driver P1 controlled by a pulse-modulated signal via control circuit 88. A suitable power driver P1 is manufactured by Micrell Corporation, model MIC4423CN. The power drivers are controlled by an optoisolator, such as model HCPL 2631, available from Hewlett Packard Corporation. The control signal to the optoisolator is provided as current loop signal generated by emitter follower (e.g. a transistor, 2N4401), which in turn is controlled by a rate/energy control signal from controller 70.

Prior to initiating the series of fast repetition flashes, flash lamp 22 has to be triggered. Trigger circuit 86 generates a high voltage, 5-15 kV spike at the output of transformer T, which is applied across the flash lamp electrodes 25 and 27 via lines 23b and 25b, which voltage spike ionizes the gas in flash lamp 22 and thus reduces the lamp impedance to few ohms. Preferably, for xenon flash lamp 22 where the required pilot arc is larger than 30 millimeters in length, external triggering is used in which the pilot arc is generated between the lamp cathode (i.e., electrode 27) and triggering electrode 25a outside the glass envelope of flash lamp 22. As shown in FIG. 1, for example, mirror 26 acts as the triggering electrode. For bulb-type flash lamps, where the required length of the arc is smaller than 8 to 10 millimeters in length, internal triggering can be used.

Triggering circuit 86 shown in FIG. 2, preferably uses power MOSFET transistors Q3, (IRFP350 from International Rectifier) to generate a triggering pulse for flash lamps 22. Additional transistors can be used to allow selective operation of one or more flash lamps using a single current switch particularly in a situation where light of different spectral quality is required, or selective illumination of different objects is required. The triggering voltage used to charge capacitor C3 is determined by Zener diodes Z3, Z4 (1N992B) and diode D4 (1N978B). Resistor R4 determines the charging rate of the capacitor C3. Capacitor C3 discharges through resister R5, diode D5 (1N4007), primary coil of the triggering transformer T (TR-180-B from EG&G), and transistor Q3. Transistor Q1 is controlled by the power driver P2 (TC4804 from Teledyne), which in turn is controlled by current loop on their terminal 2 and 3 with 3-5 mA, and 0.6 $\mu$s long pulses from controller. Diode(s) D5 ensure a selective firing of flash lamp(s) 22 assuming there is more then one flash lamp.

Rate regulating means for providing a series of fast repetition rate flashes having various rates is accomplished by the time delay between ON signals sent from controller 70 to the control circuit 88. The energy of each flash can be controlled from zero to maximum energy stored in capacitor 84 (C1-C2) by the length of the ON pulse.

Means for regulating the energy for the series of excitation flashes as well as energy for each flash is controlled using a feedback signal from the reference detector 30. The feedback signal is used to switch OFF the current switch 85 when the flash intensity reaches the level requested by the controller 70. Optionally, an arbitrary control of flashes energy may be applied in a form of arbitrary ON-OFF signals from controller 70. The arbitrary control, however, results in less reproducible flash energy, especially when linear flash lamps are used. In the preferred embodiment of the energy regulating means, an arbitrary ON-OFF signal from controller 70 determines the maximum allowable length of the flash, and feedback signal overrides the arbitrary OFF signal when the flash energy reaches the required level. A conventional feedback circuit can be designed by one skilled in the art.

The energy of each flash in the series of fast repetition rate flashes is typically controlled to be about 5% to 20% of the saturation intensity for a sample of phytoplankton or higher plant. Preferably, the energy of each flash in the series of fast repetition rate flashes is 10% of the saturation intensity and for phytoplankton this corresponds to a range of $2-5 \times 10^{12}$ quanta/cm$^2$.

The slowest repetition rate without retriggering is determined by the period of time where flash lamp is ionized following the flash. This time depends on the lamp construction and the energy of flashes, and averages at 60 to 100 $\mu$s. When longer time delay between flashes are required, the flash lamp must be retriggered. In the preferred embodiment we use a very short triggering pulse of 0.61$\mu$s. The low energy of triggering signal allows retriggering the flash lamps with up to a 10 kHz rate. Linear flash lamps with an external triggering electrode offer more reliable retriggering at such high rates than do the flashbulbs. The number of excitation flashes in the series is determined by the ratio of energy stored in the discharge capacitor (84) C1 and C2 as set by power supply 82, and is a function of the average energy used by a single flash. Generally, the number of flashes in the series includes about 10 flashes to about 100 flashes. Preferably, the number of flashes include about 32 flashes to 64 flashes and requires an initial voltage of about 400 volts stored in discharge capacitors C1 and C2, dependently on the repetition rate.

Figure 3A:
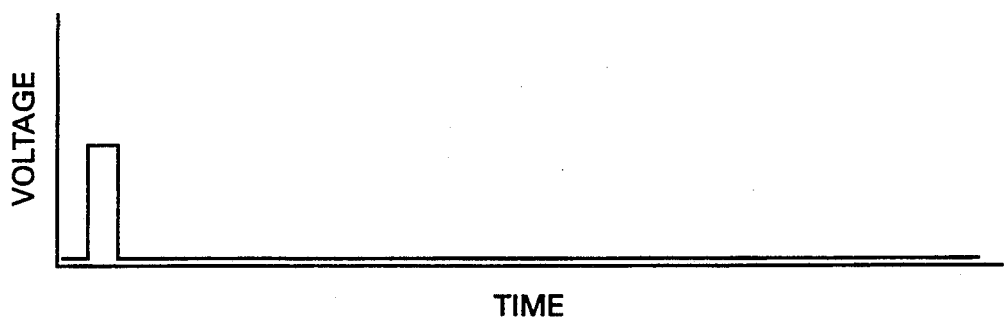
FIG. 3a, 3b and 3c are, respectively, graphical representations of a triggering signal, flash timing/intensity signal, and flash lamp output for the embodiment shown in FIG. 1.
Figure 3B:
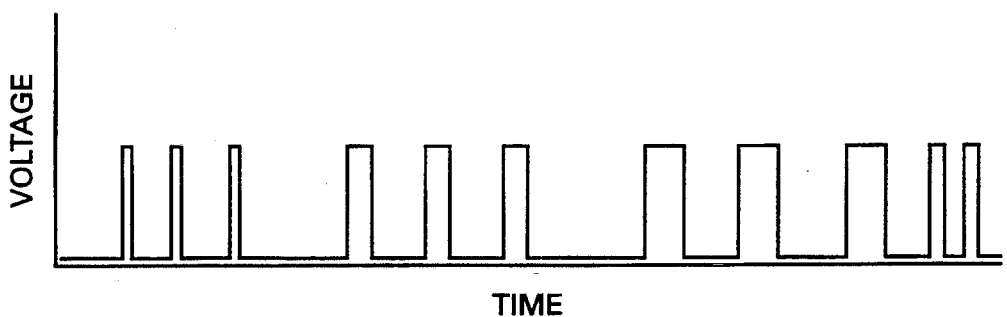
Figure 3C:
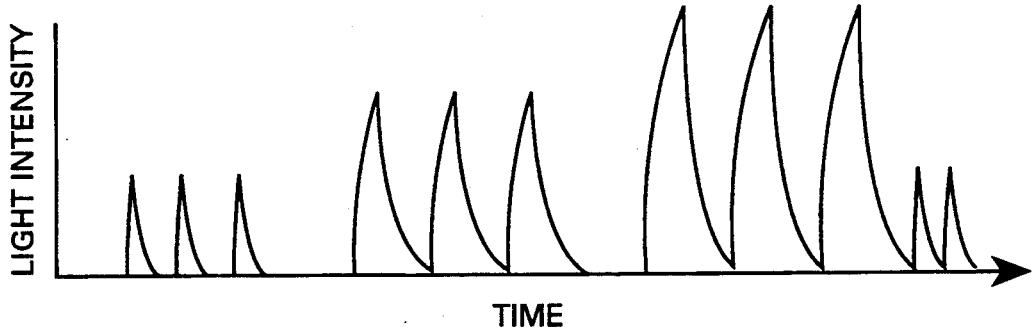

Referring now to FIG. 3a–3c, it is seen that the flasher control signals generated by flash control unit 80 are shown. Following a 0.6 μs trigger signal as shown in FIG. 3a, the flash control signals from controller 70 and flash controller 80 are used to control both the timing of the flashes and the flash intensity produced by flash lamp 22. Each flash is generated following a 200 ns delay after an ON signal (the rise time of the OFF-ON transition in the current switch), and the flash energy is proportional to the length of the ON signal. The flash light decays following the ON-OFF transition of the control signal. The decay time is defined by the ON-OFF transition in the current switch, by the lamp inductance, and by the kinetics of the gas deionization in the lamp (i.e., afterglow) (see FIG. 3b and FIG. 3c).

Because of high current levels and high switching speed, flash control unit 80 generates a significant amount of RF noise. To reduce such noise, flash control unit 80 and flash lamp 22 are enclosed in a iron enclosure Shown in the preferred embodiment in FIG. 5, cylindrical can 200 is made of soft iron to minimize the amount of RF noise generated during flashes, and in addition, all the control signals to the flasher are optoisolated.

Figure 4:
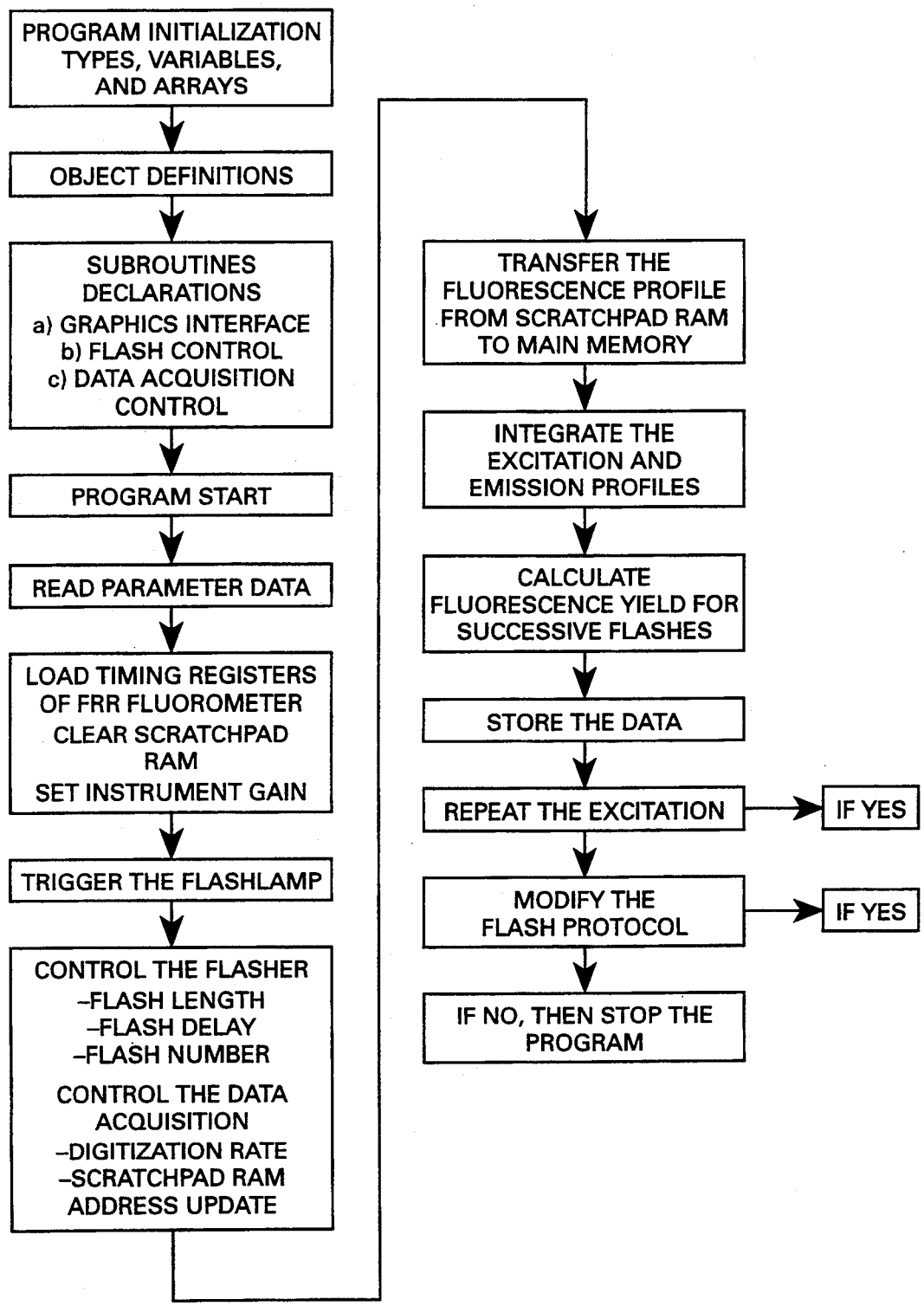
FIG. 4 is a flow diagram of the computer controlled operation of a preferred embodiment of the fast repetition rate fluorometer of the present invention.

Referring now to FIG. 4 the operation of computer 75 and controller 70 are explained as follows. In program initialization, information concerning a desired preprogrammed number of flashes, flash energy and time delay is read into timing registers of FRR Fluorometer 10. Data buffer 72 (scratchpad memory) is cleared and initialized. Prior to initialization of the flash sequence flash lamp 22 is triggered, then flash control unit 80 generates the sequence of current pulses to the flash lamp. During flashes the excitation and fluorescence signals are digitized with 10 MHz rate, and the digitized data are stored in the data buffer. After completion of the flashing sequence data are downloaded to the controller and reduced by integrating the excitation and emission profiles, and calculating fluorescence yields for successive flashes, in order to produce the photosynthetic parameters, which are then stored for later analysis. If desired the excitation cycle can be repeated or the flash protocol can be modified, before the program operation is stopped.

Figure 5:
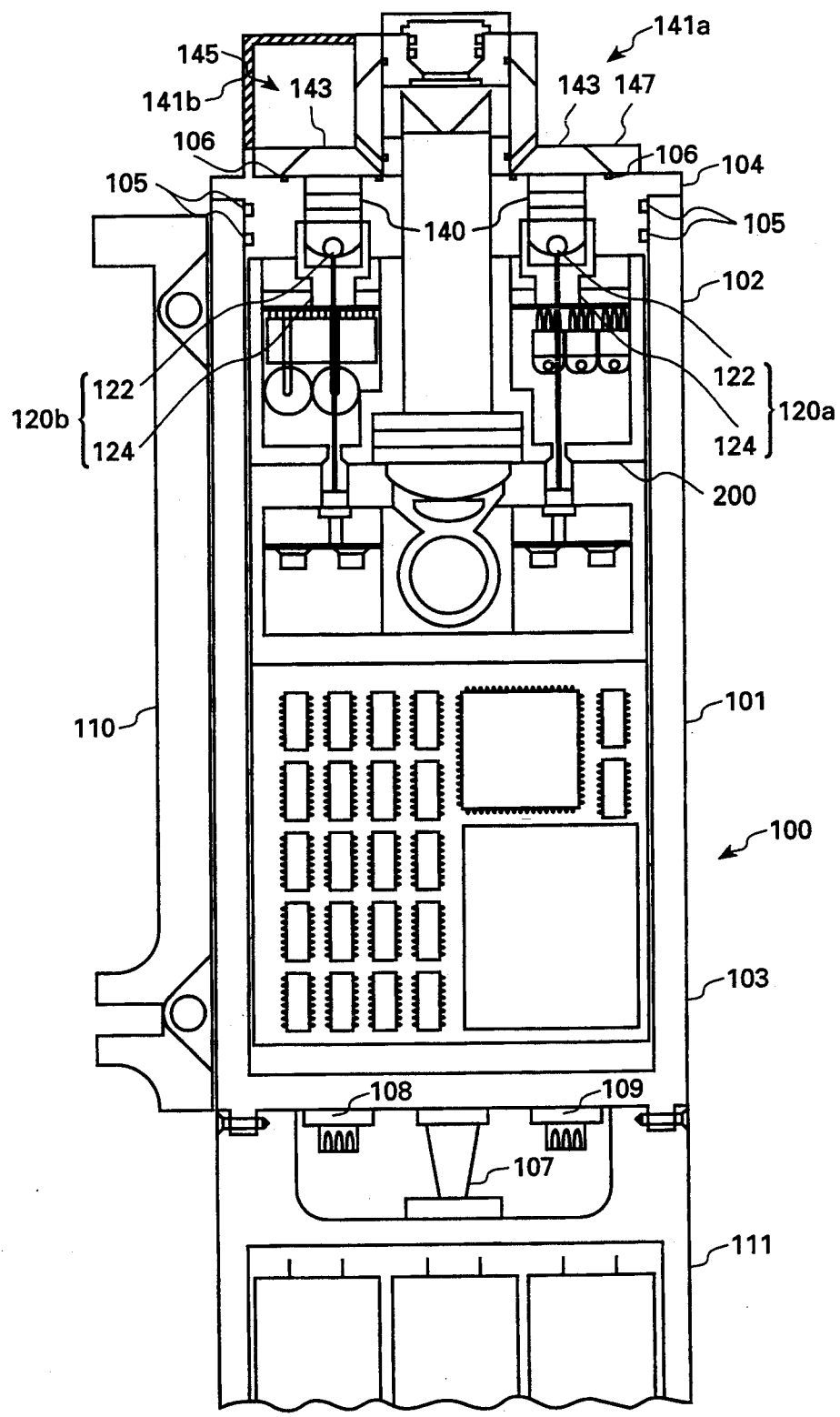
FIG. 5 is a cross-sectional, partially broken away, side elevation view of a portion of preferred alternative embodiment of a fast repetition rate fluorometer constructed according to the present invention, which includes two flash lamps and which is configured as a compactly designed and portable, submersible unit.

Although the FRR Fluorometer can be easily configured as a bench top model, a preferred embodiment of the invention for aquatic system research is a submersible model as shown in FIG. 5. Submersible FRR Fluorometer 100 is generally functionally the same as FRR Fluorometer 10 with Submersible FRR Fluorometer 100 further including a pair of flashers 120a and 120b and two corresponding sample volumes, plus operable features for in situ use in the ocean. Specifically, one sample volume indicated by the arrow 141a is exposed to ambient light around FRR Fluorometer and another sample volume indicated by the arrow 141b is covered with an opaque cap 145, and is used to measure the photosynthetic parameters of an enclosed sample in the dark. Alternatively, a second sample volume can be used to excite the phytoplankton with different spectral quality light using a different excitation filter.

Referring still to FIG. 5, Submersible FRR Fluorometer 100 electronics and optics are contained in hollow cylindrical aluminum housing 101 having an open end 102 within which components are inserted and a closed end 103. Optical head block 104 also made of aluminum provides a water-tight seal for the instrument by using a pair of O-rings 105. Block 104, in addition to holding most of the optical components for the FRR Fluorometer also provides a mechanical structure for attaching and securing of the electrical components of the fluorometer. A pair of flash lamps 122, a pair of flash lamp holders 124, and a pair of excitation filters 140 are operatively contained in block 104. The filtered excitation light from flash lamp 122 enters the sample volumes 141a and 141b via optical windows 143, custom-manufactured by ESCO Products, Inc. Optical windows 143 are made of clear fused silica material and O-rings 106 provide water-tight seals between block 104 and optical windows 143. Optical window 143 is held in place by a plastic retainer 147 made of black Delrin which is optically inert (i.e., does not fluoresce when excited by strong blue-green light).

Closed cylindrical end 103 is equipped with three submersible electrical connectors, 107, 108, and 109. Power connector 107, (Brantner XSG-4-BCL), is used to provide operating power for the instrument. The analog interface connector 108, (Brantner XSG-4-BCL) is used to output an analog signal from the instrument in the standard most accepted by the oceanographic instrumentation. The digital interface connector 109, (Brantner VSK-12-BCL) is used to communicate, program, and output data in a digital form from the fluorometer. For its profiling operation FRR Fluorometer is equipped with a hanger 110 that allows for mounting the instrument in an Oceanics rosette, in place of a water sampling bottle.

Optionally, two more connectors can be added to closed cylindrical end 103 to accommodate an external pressure sensor and external temperature sensor. A preferred temperature sensor for such use is Sea Bird model SBE-3-01. The signal from such a temperature sensor is converted from frequency to voltage using Analog Devices, Inc. ADVFC32 frequency to voltage converter, and then processed in a way similar to that used to process the PAR signal, as described above. A preferred depth sensor is SEA-Bird model SBE-29-300.

FRR Fluorometer 100, as shown in the embodiment, uses an external battery pack 111 that snaps onto cylindrical housing 101. The battery pack can be designed using a variety of battery types depending on the application: for the profiling operation we selected rechargeable batteries, and for a long-term moored application, alkaline D-cells are selected. Optionally, lithium batteries may be used where the highest power density is required. These features are important for a long-term moored application, where the instrument will operate for up to six months on a single battery pack, storing the data with a low duty cycle.

In case of a battery-powered application it is required to minimize the power consumption when the fluorometer s flasher is not active. Following firing a series flashes, the flashers discharge capacitor must be recharged, which takes about 1 second. In this time period the power for the flasher can be cut-off using the power management circuitry built around the optoisolator U2 (ILD2 from Siemens), MOSFET transistor Q9B (SI9953dY from Siliconix), and 5 V power regulator U6 (MAX666 from Maxxim). Additionally, the power for the charge power supply can be controlled by the transistor Q9A (SI9953DY from Siliconix), minimizing the power consumption when the flasher in inactive.

A. Photosynthetic Model for Measurements Obtainable by Fast Repetition Fluorometry:

While the invention is not limited to the underlying theory of photosynthesis, the following model of FRR fluorometry helps in understanding the operation of the FRR Fluorometer and its ability to measure photosynthetic parameters of a sample of phytoplankton and higher plants, based on the resulting fluorescence of a sample's Photosystem II (PSII) in response to a series of fast repetition rate excitation flashes.

Figure 6:
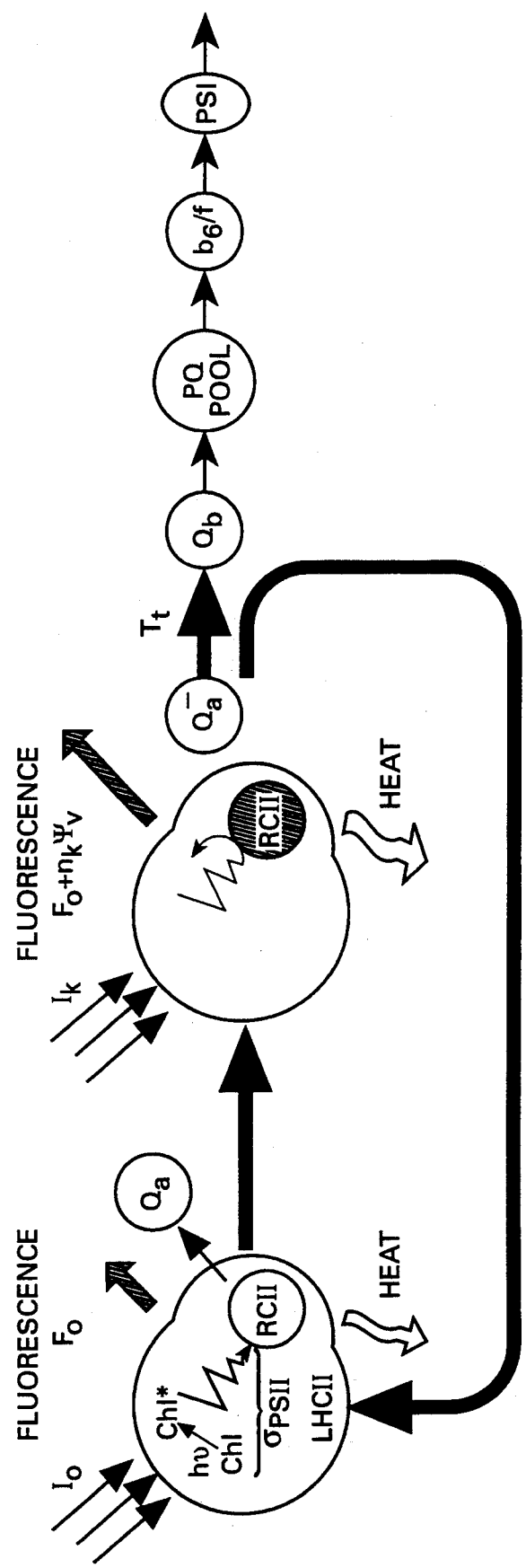
FIG. 6 is a model of Photosystem I (PSI) and Photosystem II (PSII), with the reaction center of Photosystem II shown as cycling from its opened to its closed state.

FRR fluorometry can be explained using a simplified model of PSII as shown in FIG. 6. Generally, the quanta of light generated by a series of fast repetition rate flashes is absorbed by the light absorbing pigments of PSII (LHCII) resulting in generation of the excited state of its chlorophyll molecule (Chl*), followed by the excitation transfer to the PSII reaction center (RCII). The overall efficiency of the light absorption and the excitation transfer is defined by the effective absorption cross section of PSII ($\sigma_{PSII}$). Upon arrival to an open reaction center (where $Q_A$, the first stable electron acceptor is oxidized) the excitation initiates a primary charge separation, leading to $Q_A$ reduction (closure of RCII). When in a closed state, the RCII cannot process any subsequent excitation generated by the next flash, therefore the excess of excitation energy is lost in a form of increased thermal and radiative dissipation, shown by the heat and the fluorescence arrows in FIG. 6. As a result, the observed fluorescence yield, increases in proportion to the fraction of closed reaction centers. As the $Q_A$ is being reoxidized by the process of electron transport from PSII to PSI, the PSII reaction centers will reopen, and the fluorescence yield decreases. When the PSII reaction centers are illuminated by a sequence of fast repetition flashes, the fluorescence yield changes accordingly to an equilibrium between the rate of excitation delivery to the RCII ($=[dI/dt]*\sigma_{PSII}$), and the rate of $Q_A$ oxidation ($=1/\tau_t$).

The fluorescence signal induced by FRR fluorometer protocol, F, can be generally expressed as $$F = F_o + (F_m - F_o)A = F_o + F_v A \qquad (1)$$

where $F_o$ is the fluorescence yield measured when all PSII reaction centers are open, $F_m$ is the variable fluorescence yield measured when all PSII reaction centers are closed, and A is a fraction of PSII reaction centers closed at a given state of the FRR protocol, $0 \leq A \leq 1$. The difference between $F_m$ and $F_o$, is called variable fluorescence, $F_v$, which can be expressed as a product of the concentration of photosynthetically active PSII reaction centers, $n_{PSII}$, and the quantum yield of variable fluorescence, $\Psi_v$ $$F_v = n_{PSII} \Psi_v \qquad (2)$$

$F_v$ can be clearly associated with those PSII reaction centers that are capable of transient closure and opening, i.e. conducting an photosynthetic act. $F_o$, on the other hand, is a sum of the fluorescence signal originating from the open PSII reaction centers, from PSII reaction centers that are permanently closed or disconnected from the antenna, as well as from other sources of fluorescence signal such as unattached chlorophyll, or pheopigment.

The fluorescence yield at the i-th flash of the FRR protocol, $F_i$, is determined by the fraction of closed reaction centers at the i-th flash, $A_i$. When measured in a dark ambient, $A_i$ changes are brought about by the light quanta from FRR excitation flashes. When measured under ambient light, $A_i$ is controlled by both, the background light and the FRR excitation flashes. Denoting the fraction of PSII reaction centers closed by the background light as $A_b$, then $A_1$, a fraction of the RCII that are closed following the first flash can be expressed as follow:

$$A_1 = A_b + [1 - \exp(-\sigma_{PSII} I_1)](1 - A_b), \qquad (3)$$

where the $I_1$ is the energy of the first flash, the term $1 - \exp(-\sigma_{PSII} I_1)$ describes the fraction of RCII that received at least one excitation during the first flash, and $1 - A_b$ is the fraction of RCII open prior to the first flash. $1 - A_b$ is the same as "photochemical quenching", a parameter used in the photosynthesis related literature to describe a level of fluorescence yield quenching due to the presence of PSII reaction centers.

By the time a second flash is issued, a portion of the reaction centers closed by the first flash will reopen due to electron transfer from $Q_A^-$ to the PQ pool, resulting in A decrease to a level $A = A_b + (A_1 - A_b)\exp(-\Delta t_2/\tau_t)$, where $\Delta t_2$ is the time interval between the second and first flash, and $\tau_t$ is the time constant of $Q_A^-$ reoxidation. Consequently, the fraction of closed RCII immediately following the second flash can be expressed as $$\begin{aligned} A_2 &= A_b + (A_1 - A_b)\exp(-\Delta t_2/\tau_t) + \\ &\quad [1 - \exp(-\sigma_{PSII} I_2)][1 - A_b - \\ &\quad (A_1 - A_b)\exp(-\Delta t_2/\tau_t)] = \\ &= 1 - \exp(-\sigma_{PSII} I_2)\,[1 - A_b + \\ &\quad (A_2 - A_b)\exp(-\Delta t_i/\tau_t)], \end{aligned} \qquad (4)$$

leading to a general, recursive expression $$A_i = 1 - \exp(-\sigma_{PSII} I_i)[1 - A_b + (A_{i-1} - A_b)\exp(-\Delta t_i/\tau_t)] \qquad (5)$$

with $A_o = A_b$. Substituting $A_b = 0$ into equation (5) yields an expression for the results of FRR protocol in the dark (all RCII open prior to flashes).

The fluorescence profile $F_i$ observed during FRR protocol is a function of $F_o$, $F_v$, $\sigma_{PSII}$, $\tau_t$, and $A_b$. All these parameters can be retrieved by fitting the Equations (5) and (1) into experimental data. Most of the gradient-based fitting algorithms utilize an iterative procedure of a form $$x^k = x^{k-1} - c\left[\frac{\partial F}{\partial x}(F - f)\right]\left[\frac{\partial F}{\partial x_i}\frac{\partial F}{\partial x_j}\right]^{-1}, \qquad (6)$$

where $x^{k-1}$ and $x^k$ are the vectors of searched parameters calculated at iteration $k-1$ and $k$, respectively, $x = [F_o, F_v, \sigma_{PSII}, \tau_t, A_b]_T$, F is the fit function, f is the experimental data, and $\partial F/\partial x_j$ are partial derivatives of the fit function with respect to the searched parameters. Because of the recursive character of the fit function, the partial derivatives are calculated recursively:

$$\left(\frac{\partial F}{\partial F_o}\right)_i = 1 \quad (7)$$

$$\left(\frac{\partial F}{\partial F_v}\right)_i = A_i \quad (8)$$

$$\left(\frac{\partial F}{\partial A_b}\right)_i = \left(\frac{\partial F}{\partial A}\frac{\partial A}{\partial A_b}\right)_i = F_v\left(\frac{\partial A_i}{\partial A_b}\right) = \quad (9)$$

$$F_v \exp(-\sigma_{PSII} I_i)\left[1 + \left(\frac{\partial A_{i-1}}{\partial A_b} - 1\right)\exp(-\Delta t_i/\tau_t)\right]$$

$$\left(\frac{\partial F}{\partial \sigma_{PSII}}\right)_i = \left(\frac{\partial F}{\partial A}\frac{\partial A}{\sigma_{PSII}}\right)_i = F_v\frac{\partial A_i}{\partial \sigma_{PSII}} = \quad (10)$$

$$F_v\Big\{\exp(-\sigma_{PSII} I_i)\Big[E_i(1 - A_b - $$

$$(A_{i-1} - A_b)\exp(-\Delta t_i/\tau_t) + \frac{\partial A_{i-1}}{\partial \sigma_{PSII}}\exp(-\Delta t_i/\tau_t)\Big]\Big\}$$

$$\left(\frac{\partial F}{\partial \tau_r}\right)_i = \left(\frac{\partial F}{\partial A}\frac{\partial A}{\partial \tau_t}\right)_i = F_v\frac{\partial A_i}{\partial \tau_t} = \quad (11)$$

$$F_v \exp(-\sigma_{PSII} I_i - \Delta t_i/\tau_r)\left[\frac{\Delta t_i}{\tau_t^2}(A_{i-1} - A_b) + \frac{\partial A_{i-1}}{\partial \tau_t}\right]$$

Because the fitting function is highly nonlinear, it is desirable to design a set of experimental protocols so that the number of the searched parameters can be reduced, or the fit function may become more sensitive to some of the parameters, at the cost of the other. The FRR experiment conducted at dark will require four parameters to be fit ($A_b=0$), and the fit function will become critically sensitive to the $F_o$ parameter. If the flashes are applied at high repetition rate so that $\Delta t_i/\tau_t \sim 0$ then $Q_A^-$ cannot be reoxidized between flashes, and Equation (5) further simplifies to a form $$A_i = \quad (12)$$

$$1 - \exp(-\sigma_{PSII} E_i)(1 - A_{i-1}) = 1 - \exp\left(-\sigma_{PSII}\sum_{j=1}^{j=i} I_j\right),$$

independent on $\tau_t$. Usually the pumping protocol conducted in the dark is used to estimate $F_o$, $F_v$, and $\sigma_{PSII}$. These parameters are then fixed during the analysis of the data obtained under ambient light with lower repetition rate to calculate $A_b$ and $\tau_t$.

Using equations (1) and (5) we develop a methodology to completely characterize the phytoplankton photosynthetic performance. To estimate the photosynthetic parameters with optimal signal-to-noise ratio, the methodology requires measuring the fluorescence yield changes in response to fast repetition flashes, $F_i$, both in a dark ambient, and under ambient illumination. To accomplish this simultaneously, the submersible embodiment of FRR fluorometer (see FIG. 5) is equipped with two sample chambers: one chamber is exposed to ambient light, and the other chamber is kept in darkness.

To optimize the process of retrieving the photosynthetic parameters from $F_i$ data, the FRR fluorometer operates in three different modes: pumping mode, saturation mode, and relaxation mode. The pumping mode is used to estimate the variable fluorescence, $F_v$, the fraction of closed reaction centers (RCII) under ambient illumination, $A_b$, and the absorption cross-section of PSII ($\sigma_{PSII}$). The saturation mode yields information on the saturation level of photochemical quenching, the level of electron cycling around PSII, and the size of the PQ pool. The relaxation mode is used to estimate the rate of electron transfer between $Q_A$ and the PQ pool and the turnover time of photosynthesis.

In the pumping mode (FIG. 7), excitation flashes of energy of $\sim 5 \times 10^{12}$ quanta*cm$^{-2}$ are applied at a 100,000 to 250,000 Hz repetition rate. Each flash results in excitation of a fraction of PSII reaction centers described by the product of the flash intensity and the effective absorption cross section of PSII ($\sigma_{PSII}$). The excited reaction centers undergo the process of charge separation, followed by electron transport from Photosystem II (PSII) to Photosystem I (PSI). Because of limited rate of electron transport ($\tau_Q = 160$–300 $\mu$s), most of the reaction center excited by a given flash cannot accept the excitation generated by subsequent flashes. The excess of excitation energy is wasted as heat and fluorescence, leading to an increase in the observed fluorescence signal.

In the saturation mode (FIG. 8), flashes of $\sim 10\%$ saturation intensity are applied at about 100 to 200 $\mu$s intervals which corresponds to a rate of 5,000 to 10,000 Hz. Each excitation flash will temporarily close a fraction of the PSII reaction centers. Between flashes, most of the closed reaction centers will reopen due to the fast ($\sim 160$–300 $\mu$s) electron transfer from $Q_A^-$ to the PQ pool. This will keep fluorescence yield at a level close to $F_o$ (or $F_a$, when measured under ambient light), until the PQ pool is significantly reduced. Since the PQ pool oxidation time constant is in range of 4–10 ms, the saturation cycle will eventually lead to reduction of the PQ pool. Once the PQ pool is reduced, the fast reoxidation of $Q_A^-$ between flashes will no longer be possible. Subsequent excitation flashes will close more and more reaction centers and the fluorescence yield will increase. The rate of increase of the fluorescence yield will be proportional to the intensity of the excitation flashes, and the absorption cross section of PSII. The capacity of the PQ pool may be calculated from $\sigma_{PSII}$ and the cumulative energy of excitation flashes absorbed before the fluorescence rises. Another estimate of the PQ pool size is the ratio of excitation energy required to saturate fluorescence yield in the saturation protocol to the excitation energy required to saturate fluorescence yield in the pumping protocol.

The fluorescence yield at the end of the saturation sequence will be less than that at the end of pumping sequence. Due to much faster excitation rate, the pumping sequence will be completed after accumulating a single electron in $Q_A$, where there is no limitation from the electron donor part of PSII. In the saturation mode there will be as many electron turnovers before fluorescence saturation as the size of PQ pool. Because of the limited turnover of the electron donor portion of PSII a cyclic electron flow around PSII will be observed. Such a mechanism will provide a wasteful pathway for oxidizing $Q_A$ resulting in a decrease of $F_v$ level in the saturation mode as compared to the pumping mode.

The yield of electron cycling around PSII, $\Phi_{cyc}$ can be calculated as $$\Phi_{cyc} = 1 - F_{v,sat}/F_{v,pump}, \quad (13)$$

where $F_{v,sat}$ is the variable fluorescence yield measured in the saturation protocol, and $F_{v,pump}$ is the variable fluorescence yield measured in pumping protocol. Consequently, the yield of electron transport from $Q_A$ to the Photosystem I and to terminal electron acceptor can be calculated as $$\Phi_e = F_{v,sat}/F_{v,pump}. \quad (14)$$

The pumping and saturation modes will be followed by the relaxation mode. In the relaxation mode (FIG. 9) both the intensity of the excitation flashes and their repetition rate will be lowered, allowing PSII to relax to its initial level. When a relaxation mode is applied after the pumping mode, the observed fluorescence decay ($\tau \sim 160$–$300$ $\mu$s) reflects the kinetics of electron transport from $Q_A^-$ to the PQ pool. When a relaxation mode is applied after the saturation mode, the observed fluorescence decay reflects the kinetics of PQ pool oxidation (3–10 ms), which is the same as the turnover time of photochemistry ($\tau_p$).

The FRR fluorometer also allows measurements of the concentration of the PSII active reaction centers in the bulk chlorophyll, $n_{PSII}$. This parameter is highly sensitive to such environmental factors as nutrients and trace metal availability, excessive irradiance, and UV exposure. Assuming that the quantum yield of variable fluorescence is constant (when measured in the absence of nonphotochemical quenching following some period of dark adaptation), $n_{PSII}$ can be estimated from Equation (2) as $$n_{PSII} = F_v/\Phi_v. \quad (15)$$

Using the photosynthetic parameters calculated from FRR fluorometry data it is possible to estimate the primary productivity, or the rates of photosynthesis under given irradiance, $P_E$:

$$P_E = E\sigma_{PSII}(1-A_b)\Phi_e n_{PSII}, \quad (16)$$

where E is a measured PAR signal. The yield of electron transport, $\Phi_e$, can either be calculated from Equation (14), or alternatively, estimated from a relationship between the rate of $Q_A$ reduction, $P_{Qred}$, and the turnover time of photosynthesis calculated from the relaxation protocol:

$$\Phi_e \sim 1 \text{ for } P_{Qred} < = 1/\tau_P \quad (17)$$

$$\Phi_e \sim (P_{Qred}\tau_P)^{-1} \text{ for } P_{Qred} > 1/\tau_P. \quad (18)$$

where $$P_{Qred} = E\sigma_{PSII}(1-A_b). \quad (19)$$

B. Operation Modes of the Fast Repetition Rate Fluorometer and Measurements of Photosynthetic Parameters The FRR fluorometer is operable in three different modes: a pumping mode in which a series of fast repetition rate flashes is fast enough to incrementally and gradually close substantially all the PSII reaction centers from a sample of phytoplankton or higher plant contained in a sample volume, prior to the PSII reaction centers ability once closed to reopen; a saturation mode in which a series of fast repetition rate flashes is not fast enough to close all the reaction centers but permits incremental filling of the PQ pool; and a relaxation mode which is performed after all the reaction centers are closed (i.e., after the pumping mode or saturation mode, or even single excitation flash of sufficient energy) and wherein the rate of the flashes and their energies is reduced to allow reopening of PSII reaction centers. The various modes permit the measurement of different photosynthetic parameters. Specifically, the pumping mode is used to estimate the photochemical quenching ($Q_p$), the effective absorption cross-section of PSII ($\sigma$PSII), the variable fluorescence ($F_v$), and the concentration of PSII reaction centers ($n_{PSII}$). The saturation mode yields information on the saturation level of photochemical quenching and the PQ pool size. The relaxation mode is used to estimate the rate of electron transfer between $Q_A$ and the PQ pool ($\tau_Q$), and the turnover time of photosynthesis ($\tau_P$).

B1. Pumping Mode

Figure 7A:
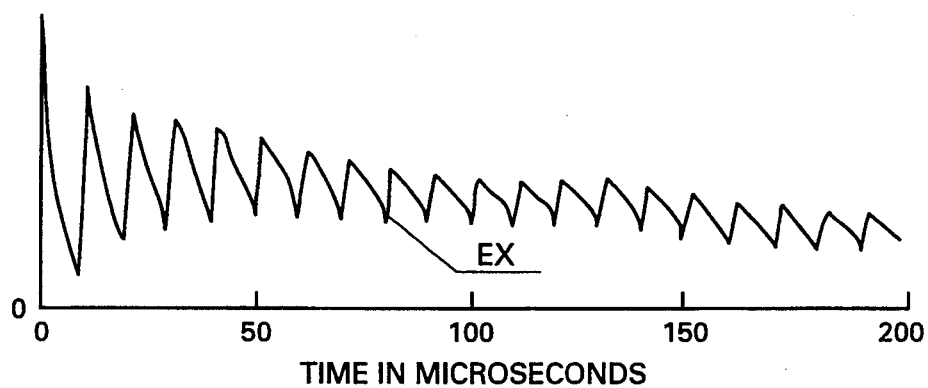
FIG. 7a–c graphically display, respectively, the traces over a 200 $\mu s$ pumping sequence of the excitation flashes (Ex), excitation flashes (Ex) relative to fluorescence (Em), and the ratio of the fluorescence over the excitation (Em/Em) (relative units) of an in vivo photosynthetic sample measured with the fluorometer of the invention.

In the pumping mode the FRR fluorometer produces a series of fast repetition rate flashes to incrementally and gradually close substantially all the PSII reaction centers from a sample of marine algae or higher plant contained in a sample volume, prior to the PSII reaction centers ability once closed to reopen. Shown in FIG. 7a-7c are examples of excitation/emission traces of the pumping mode over a 200 $\mu$s sequence as detected by the FRR Fluorometer with FIG. 7a a trace of the excitation flashes, FIG. 7b a trace of both the excitation and emissions flashes, and FIG. 7c a trace of the ratio of emission over the excitation.

As described above, in the pumping mode, the flash controller provides pulses of current of specified time duration in the range of 0.6 to 2.5 $\mu$s (halfwidth) and repetition rates of 100 to 250 kHz (i.e., 4 to 10 $\mu$s between flashes) to the flash lamp (22 in FIG. 1). The energy of the flashes during the pumping mode is constant and selected at approximately an energy of $5 \times 10^{12}$ quanta*cm$^{-2}$ which corresponds to approximately 10% saturation intensity or activation of about 10% of the PSII reaction centers of the plant or phytoplankton at the first flash, with subsequent flashes exciting another 9% (i.e. the 10% of the remaining, unexcited reaction centers), 8.1%, 7.29%, . . . and so on reaction centers. The saturation intensity is dependent on the circumstances such as nutrient and trace metal availability, and growth irradiance.

Figure 7B:
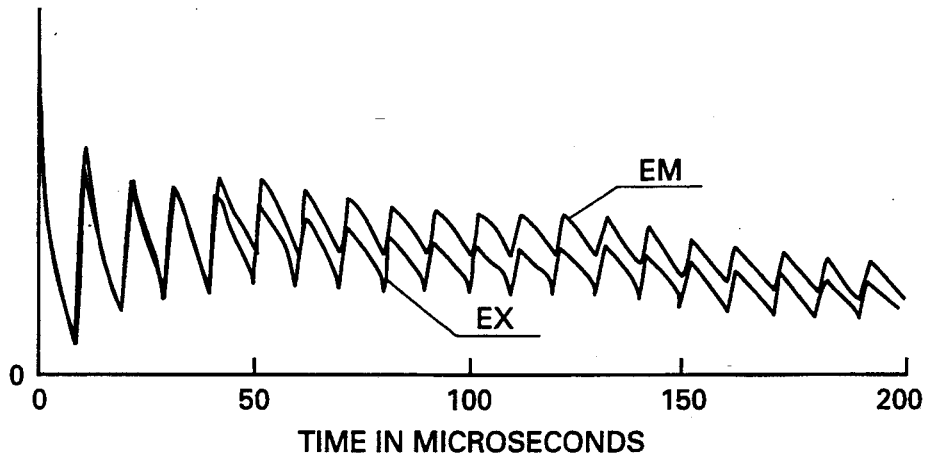
Figure 7C:
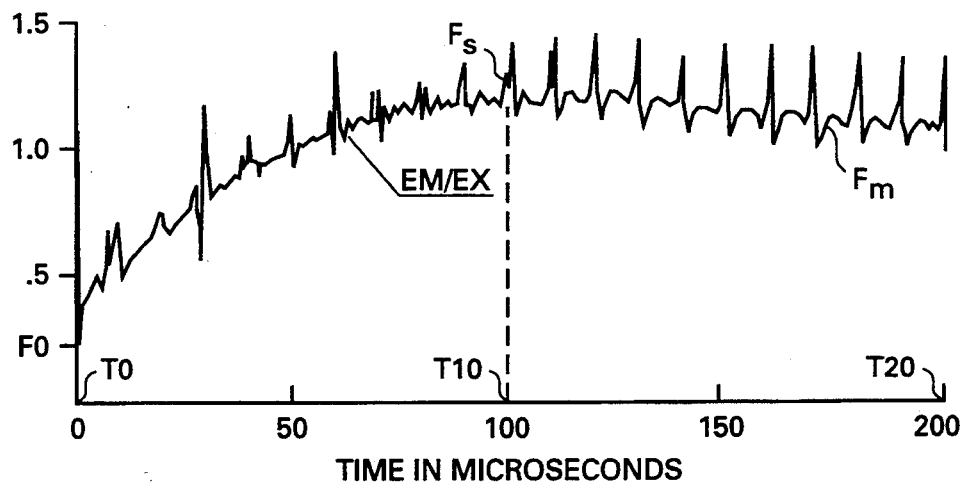

Referring now to FIGS. 7b and 7c, it is observed that the fluorescence yield measured as the ratio of emission signal (EM) to the excitation signal (EX) increases from its minimum value, $F_O$, at T0 to, $F_S$, at T10 and then levels out from T10 to T20.

The shape of the saturation curve of the fluorescence yield follows Equation (5), with the rate of saturation proportional to the energy of the excitation flashes in the pumping mode and to the effective absorption cross section of PSII, and eventually saturates at $F_m$ level. Thus, parameters $F_o$, $F_V$, and $\sigma_{PSII}$ can be estimated by fitting Equation (5) to the observed fluorescence $F_i$. Then $n_{PSII}$ can be calculated from Equation (15).

B2. Saturation Mode

Figure 8:
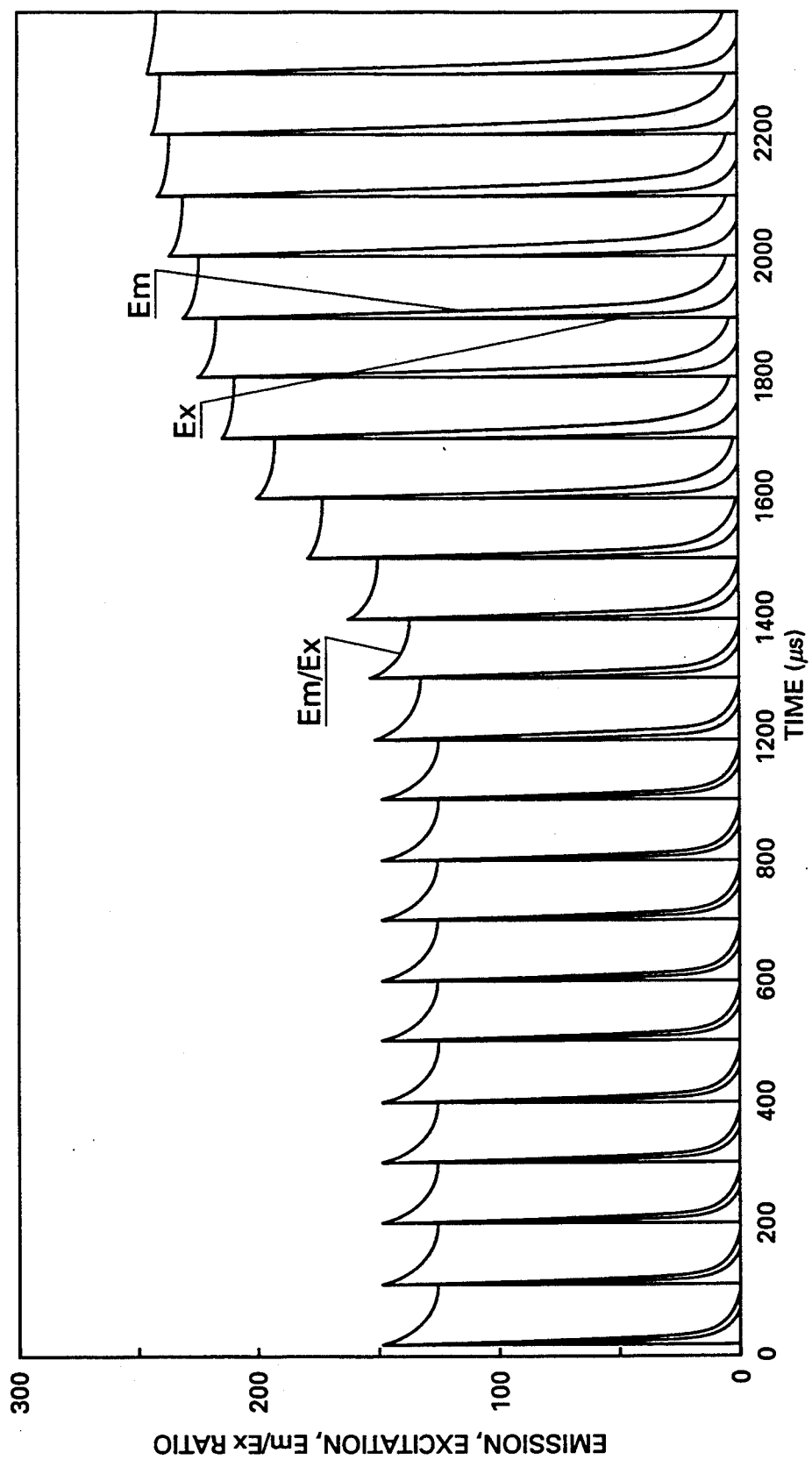
FIG. 8 graphically displays the traces over a 220 $\mu s$ saturation sequence of PSII resulting from excitation of a photosynthetic sample with flashes and producing fluorescence as measured by the fluorometer of the invention.

In the saturation mode the FRR Fluorometer flash lamp provides a series of fast repetition rate excitation flashes, at a lower repetition rate than the pumping mode, to temporarily close a percentage of the PSII reaction centers from a sample of plant or phytoplankton contained in the sample volume, with the PQ Pool gradually filling up and saturating resulting in an observed increase in fluorescence. Shown in FIG. 8 is an example of excitation/emission traces of the saturation mode over a 2400 $\mu s$ sequence as detected by the FRR Fluorometer with traces of excitation, emission, and the ratio of emission over the excitation.

As described above, in the saturation mode, the flash controller provides pulses of current of specified time 0.6 to 2.5 $\mu s$ (halfwidth) and repetition rates of 10 to 20 kHz (i.e., 50 to 100 $\mu s$ between flashes) to the flash lamp. The energy of the flashes during the pumping mode is constant and selected at 10 to 20% of saturation intensity.

The time delay between flashes in the saturation mode, 100 $\mu s$, is comparable with the time it takes for the reaction centers to reopen between flashes, permitting most of the closed reaction centers to reopen due to the fast ($\sim 160$–300 $\mu s$) electron transfer from $Q_A^-$ to the PQ pool. This will keep fluorescence yield at a level close to $F_a$ (or $F_o$ when measured in the dark), until the PQ pool is significantly reduced. Since the PQ pool oxidation time constant is in range of 4–10 ms, the saturation cycle will eventually lead to reduction of the PQ pool. Once the PQ pool is reduced, the fast reoxidation of $Q_A^-$ between flashes will no longer be possible. Subsequent excitation flashes will close more and more reaction centers and the fluorescence yield will increase.

The rate of increase of the fluorescence yield following PQ pool saturation will be proportional to the intensity of the excitation flashes, and the absorption cross section of PSII ($\sigma_{PSII}$). The capacity of the PQ pool may be calculated from $\sigma_{PSII}$ and the cumulative energy of excitation flashes absorbed before the fluorescence rise. Another estimate of the PQ pool size is the ratio of flashes before the fluorescence rise to the number of additional flashes required to fully saturate the fluorescence yield.

The fluorescence yield at the end of the saturation sequence will be less than that at the end of pumping sequence. Due to much faster excitation rate, the pumping sequence will be completed after accumulating a single electron in $Q_A$, and no limitation on reduction of P680+ will be imposed. In the saturation mode there will be as many electron turnovers before fluorescence saturation as the size of PQ pool. As a result, the reduction rate of P680+ may become limited by the turnover time of the water splitting system. This will promote a cyclic electron flow between $Q_A^-$ and P680+, providing an effective mechanisms of $Q_A^-$ oxidation. Such a mechanism will lower the level of QA reduction, and subsequently, the fluorescence yield. The difference in the fluorescence yield at the completion of the pumping and saturation cycles will indicate the rate of cyclic electron flow in PSII.

B3. Relaxation Mode

The relaxation mode can follow either the pumping mode or saturation mode. In the relaxation mode both the intensity of the excitation flashes and their repetition rate will be lowered, allowing a PSII which is saturated (either due to the pumping mode of the saturation mode) to relax to its initial level. Shown in FIG. 9 is a graphical representation of the relaxation mode.

Figure 9:
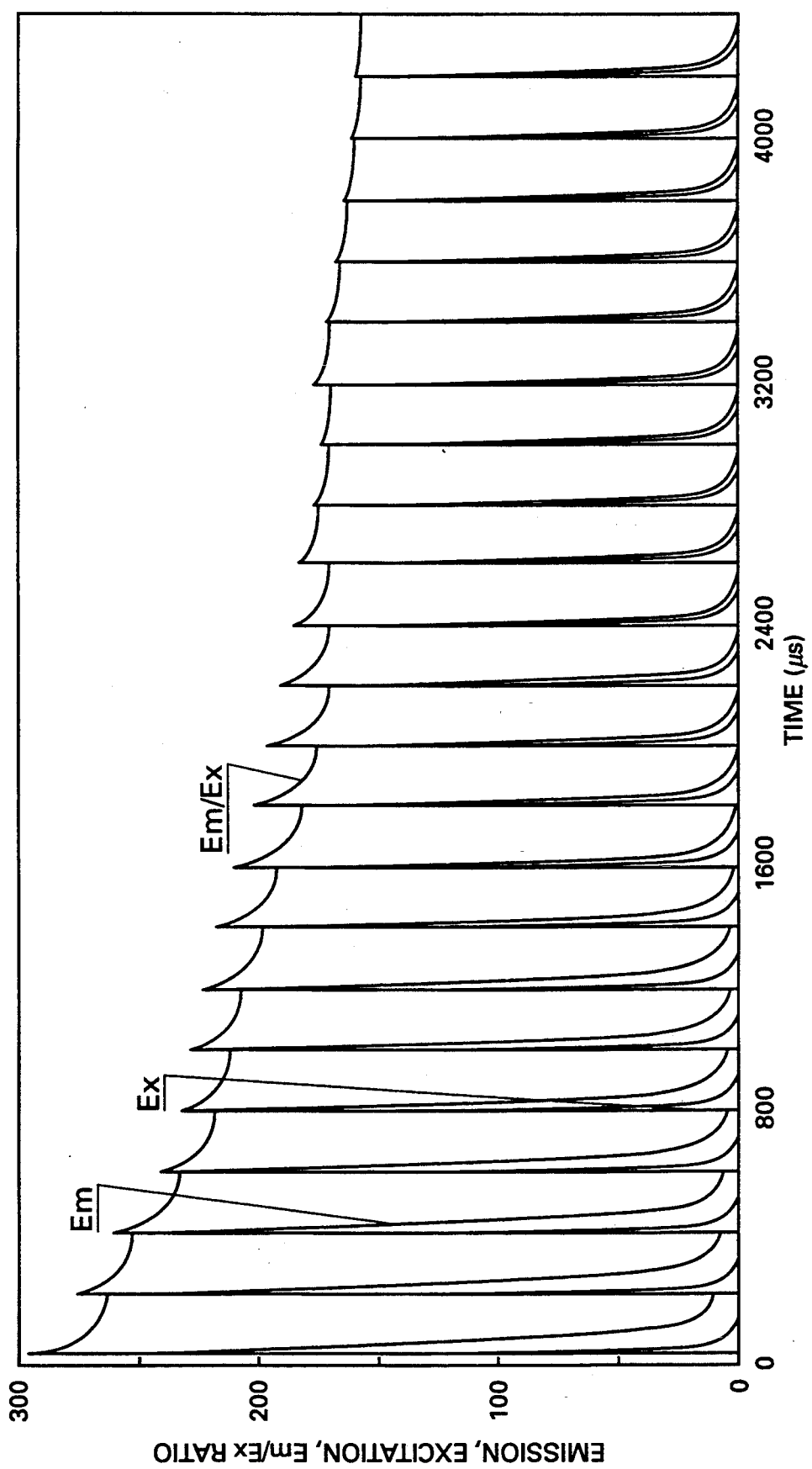
FIG. 9 graphically displays the results of relaxation.
Figure 10:
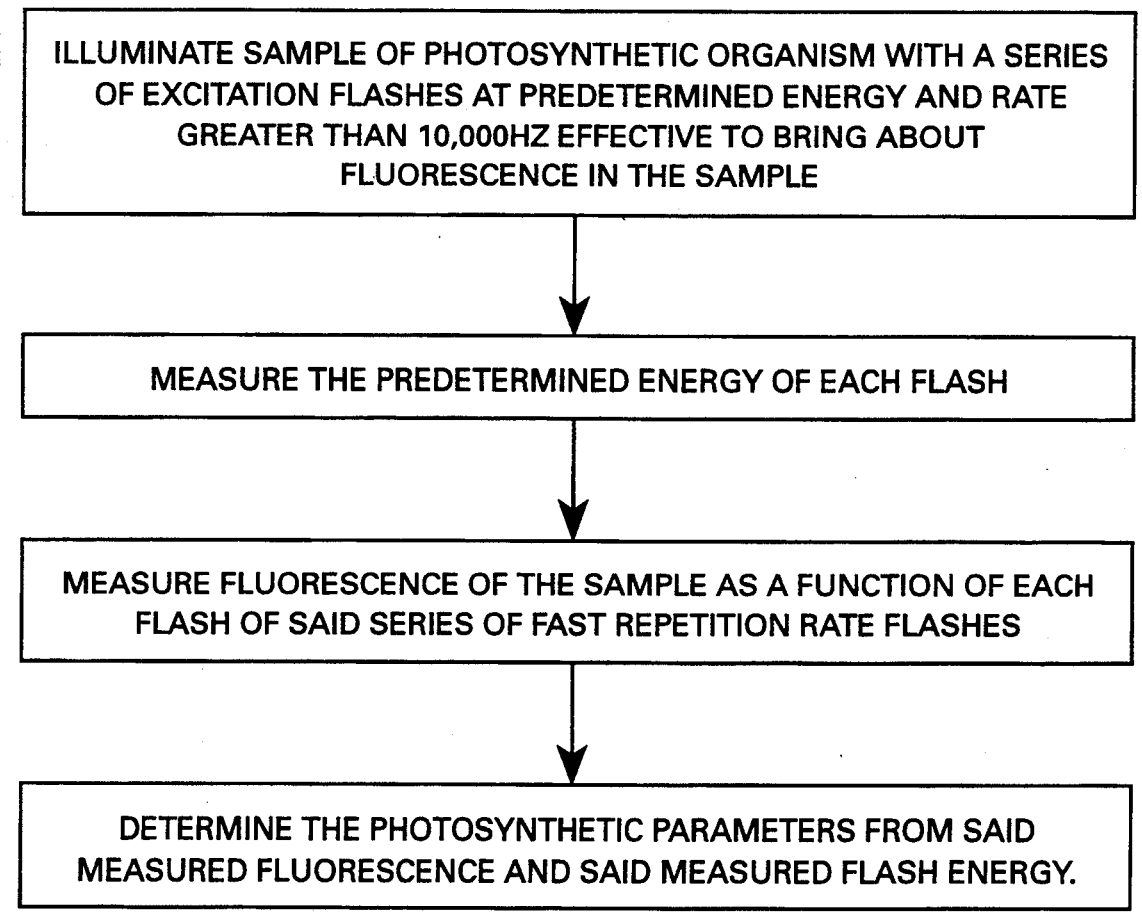
FIG. 10 is a flow chart illustrating the method of the invention.

Referring to FIG. 9, the relaxation mode is applied following the saturation mode. In this case the observed fluorescence decay reflects the kinetics of PQ pool oxidation (3–10 ms), which is the same as the turnover time of photochemistry ($\tau_p$), and is shown on the graph as EM/EX. If the relaxation mode is applied following the pumping mode(no FIG. shown). The observed fluorescence decay ($\tau \sim 160$–300 $\mu s$) reflects the kinetics of electron transport from $Q_A^-$ to the PQ pool.

What is claimed is:

1. A fast repetition rate fluorometer for measuring fluorescence of a sample of phytoplankton or higher plant in either essential darkness or under background illumination, comprising:

flashing means for producing a series of excitation flashes at a predetermined energy per flash in the range of about 5% to about 20% of the energy required to saturate the photosynthesis in the sample and at rate of greater than 10,000 Hz effective to bring about fluorescence in the sample; and first measuring means for measuring fluorescence of the sample as a function of said series of excitation flashes.

2. The fast repetition rate fluorometer as defined in claim 1, wherein said flashing means further comprises rate regulating means for providing a substantially uniform rate of said excitation flashes.

3. The fast repetition rate fluorometer as defined in claim 1, wherein said flashing means further comprises rate regulating means for providing said rate of excitation flashes in the range of about 10,000 Hz to about 250,000 Hz.

4. The fast repetition rate fluorometer as defined in claim 1, wherein said flashing means further comprises rate regulating means for providing said rate of excitation flashes in the range greater than about 10,000 Hz.

5. The fast repetition rate fluorometer as defined in claim 1, wherein said flashing means further includes rate regulating means for providing said rate of excitation flashes in the range of about 10,000 Hz to 250,000 Hz.

6. The fast repetition rate fluorometer as defined in claim 2, wherein said flashing means further comprises controlling means for controlling said series of excitation flashes to include about 10 flashes to about 100 flashes.

7. The fast repetition rate fluorometer as defined in claim 2, wherein said flashing means further comprises controlling means for controlling said series of excitation flashes to include about 32 flashes to about 64 flashes.

8. The fast repetition rate fluorometer as defined in claim 6, wherein said flashing means further comprises energy regulating means for providing a substantially uniform energy for each flash in said series of fast repetition rate flashes.

9. The fast repetition rate fluorometer as defined in claim 6, wherein said flashing means further comprises energy regulating means for providing energy for each flash in the range of about 5% to about 20% of the energy required to saturate the sample.

10. The fast repetition rate fluorometer as defined in claim 6, wherein said flashing means further comprises energy regulating means for providing energy for each flash which is about 10% of the energy required to saturate Photosystem II in the sample.

11. The fast repetition rate fluorometer as defined in claim 1, further comprising a second measuring means for measuring said energy of said series of excitation flashes.

12. The fast repetition rate fluorometer as defined in claim 11, for rapidly and accurately making measurements of various photosynthetic parameters, including ranges of variable fluorescence, effective absorption cross-section, decay kinetics of variable fluorescence, levels of energy transfer between Photosystem II units, the size of the PQ pool, and concentration of PSII reaction centers, of said sample, further comprising, electronic means operatively connected to said first and second measuring means to make said measurements.

13. The fast repetition rate fluorometer as defined in claim 11, further including a second flashing means for producing a second series of excitation flashes at a second predetermined energy per flash and at a rate of greater than 10,000 Hz to effect fluorescence in a second sample, said second flashing means being arranged in operating relationship to said measuring means for measuring the fluorescence of the second sample as a function of said series of excitation flashes.

14. The fast repetition rate fluorometer as defined in claim 13, further comprising a water-tight housing surrounding said flashing means and said first and second measuring means for submersible operation of said fluorometer.

15. The fast repetition rate fluorometer as defined in claim 1, wherein said flashing means consists of a single flash lamp.

16. A method for measuring phytoplankton or higher plants photosynthetic parameters including ranges of variable fluorescence, effective absorption cross-section, decay kinetics of variable fluorescence, levels of energy transfer between Photosystem II units, and the size of the PQ pool, comprising the steps of:
    illuminating a sample of phytoplankton or higher plants with a series of excitation flashes at a predetermined energy per flash in the range of about 5% to about 20% of the energy required to saturated the photosynthesis in the sample and at a rate 10,000 Hz to effect fluorescence in the sample;
    measuring said predetermined energy of said flashes;
    measuring fluorescence of the sample as a function of said series of fast repetition rate flashes; and
    determining said photosynthetic parameters from said measured fluorescence and said measured flash energy.

17. The method of claim 16, wherein said rate is made substantially uniform.

18. The method of claim 17, wherein said rate of excitation flashes is made to be in a range of about 10,000 Hz to about 250,000 Hz.

19. The method of claim 18, wherein said rate of excitation flashes is made to be greater than about 100,000 Hz.

20. The method of claim 19, wherein said rate of excitation flashes is made to be in a range of about 100,000 Hz to 250,000 Hz.

21. The method of claim 16 wherein said series of excitation flashes is made to have about 10 flashes to about 100 flashes.

22. The method of claim 21 wherein said series of excitation flashes is made to have about 32 flashes to about 64 flashes.

23. The method of claim 21 wherein said predetermined energy per flash is made substantially uniform.

24. The method of claim 16 wherein said predetermined energy per flash is made to be about 10% of the energy required to saturate the sample.

25. The method of claim 16, wherein said rate and said predetermined energy is made to effectively and gradually fill the PQ pool of the sample.

26. The method of claim 25, wherein said rate of excitation flashes is made to be in a range of about 10,000 Hz to about 20,000 Hz.

27. The method of claim 16, wherein said rate and energy is effective to gradually fill and saturate the sample prior to filling the PQ pool of the sample.

28. The method of claim 27, wherein said rate of excitation flashes is made to be in a range of about 100,000 Hz to about 250,000 Hz.

* * * * *